United States Patent
Hagness et al.

(10) Patent No.: US 10,492,860 B2
(45) Date of Patent: Dec. 3, 2019

(54) MICROWAVE ABLATION ANTENNA SYSTEM WITH TAPERED SLOT BALUN

(71) Applicant: Wisconsin Alumni Research Foundation, Madison, WI (US)

(72) Inventors: Susan C. Hagness, Madison, WI (US); Nader Behdad, Oregon, WI (US); Hung Thanh Luyen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 433 days.

(21) Appl. No.: 15/454,218

(22) Filed: Mar. 9, 2017

(65) Prior Publication Data

US 2018/0256251 A1    Sep. 13, 2018

(51) Int. Cl.
  *A61B 18/18*     (2006.01)
  *A61B 18/00*     (2006.01)
  *H05B 6/72*      (2006.01)

(52) U.S. Cl.
  CPC ............... *A61B 18/1815* (2013.01); *A61B 2018/00577* (2013.01); *A61B 2018/1838* (2013.01); *A61B 2018/1861* (2013.01); *A61B 2018/1892* (2013.01); *H05B 6/72* (2013.01)

(58) Field of Classification Search
  CPC ...... A61B 18/1815; A61B 2018/00577; A61B 2018/1838; A61B 2018/1861; A61B 2018/1892; H05B 6/705; H05B 6/72; H05B 6/664; H05B 6/701; H05B 6/702; H05B 6/70; H05B 6/64; H05B 6/6447; H05B 1/025; H01Q 13/08; H01Q 5/48
  See application file for complete search history.

(56) References Cited

U.S. PATENT DOCUMENTS

| 3,013,226 A | 12/1961 | Hamel et al. |
| 5,300,099 A | 4/1994 | Rudie |
| 5,683,382 A | 11/1997 | Lenihan |

(Continued)

OTHER PUBLICATIONS

Luyen et al., A Minimally Invasive, Coax-Fed Microwave Ablation Antenna with a Tapered-Slot Balun, IEEE International Symposium on Antennas and Propagation/USNC-URSI National Radio Science meeting, Jun. 26, 2016, Puerto Rico.

(Continued)

*Primary Examiner* — Jaymi E Della
*Assistant Examiner* — Rachel A. Vierra
(74) *Attorney, Agent, or Firm* — Bell & Manning, LLC

(57) ABSTRACT

A balun includes a center conductor, a dielectric material, a tapered wall, a ring, and a prong. The center conductor extends a length of the balun. The dielectric material surrounds the center conductor along the length of the balun. The tapered wall forms a portion of a tube between a first wall and a second wall. The first wall is opposite the second wall. The tapered wall is formed of a conductive material. The portion of the tube forms a slot exposing the dielectric material. The ring connects to the second wall of the tapered wall and is formed of the conductive material. The ring forms a tube surrounding the center conductor and the dielectric material. The prong connects to the ring to extend toward the first wall and is formed of the conductive material. The prong extends over a portion of the dielectric material exposed by the slot.

20 Claims, 28 Drawing Sheets

(56) References Cited

U.S. PATENT DOCUMENTS

| | | |
|---|---|---|
| 5,973,653 A | 10/1999 | Kragalott et al. |
| 6,051,018 A | 4/2000 | Larsen |
| 2007/0043346 A1* | 2/2007 | Cronin .................. A61B 18/18 606/33 |
| 2014/0358140 A1 | 1/2014 | Emmons |
| 2015/0250540 A1 | 9/2015 | Behdad |

OTHER PUBLICATIONS

Luyen et al., A Minimally Invasive, Coax-fed Microwave Ablation Antenna With a Tapered-Slot Balun, Conference slides, IEEE International Symposium on Antennas and Propagation/USNC-URSI National Radio Science meeting, Jun. 26, 2016, Puerto Rico.
Brace et al., Dual-slot antennas for microwave tissue heating: Paramet-ric design analysis and experimental validation, Med. Phys., vol. 38, Jul. 2011, pp. 4232-4240.
R.W. Klopfenstein, A transmission line taper of improved design, Proceedings of the IRE, vol. 44. No. 1, 1956, pp. 31-35.
Choi et al., Development of a novel tapered balun for the UWB UHF coupler, IEEE Power Modulator Symp., 2004, pp. 493-496.
Duncan et al., 100:1 bandwidth balun transformer, Proceedings of the IRE, vol. 48, 1960, pp. 156-164.
Ito et al., Thin applicator having coaxial ring slots for interstitial microwave hyperthermia, IEEE AP-S Antennas Propagation Soc. Int. Symp. Dig., vol. 3, 1990, pp. 1233-1236.
International Search Report and Written Opinion for PCT/US2018/067469, dated Apr. 18, 2019.

\* cited by examiner

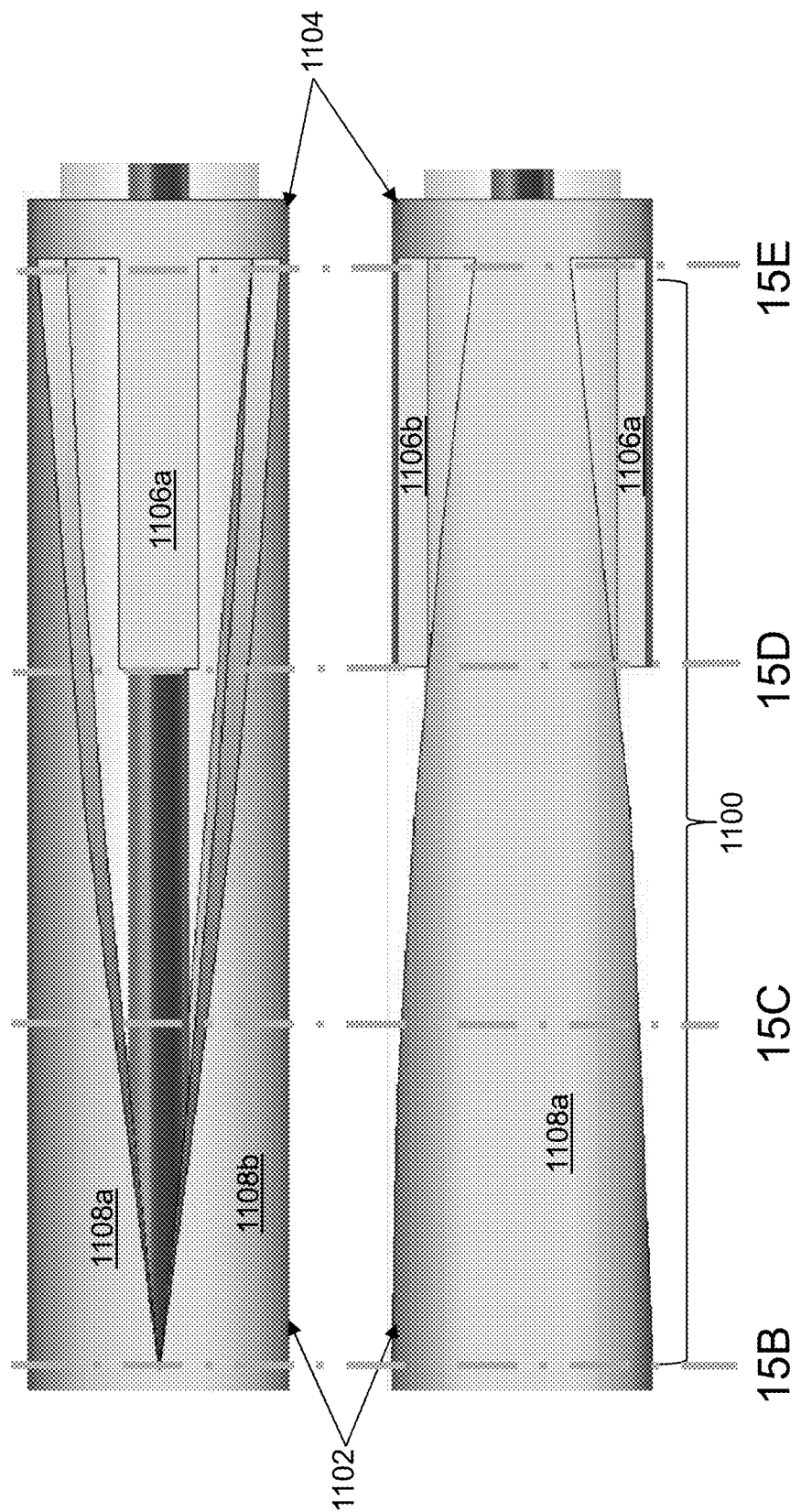

MICROWAVE ABLATION ANTENNA SYSTEM WITH TAPERED SLOT BALUN

REFERENCE TO GOVERNMENT RIGHTS

This invention was made with government support under ECCS-1406090 awarded by the National Science Foundation. The government has certain rights in the invention.

BACKGROUND

Microwave ablation (MWA) is a form of thermal ablation used in interventional radiology to treat cancer. MWA uses electromagnetic waves in the microwave energy spectrum (300 megahertz to 300 gigahertz) to produce tissue-heating effects, i.e., to heat tumors to cytotoxic temperatures. MWA is generally used for minimally invasive treatment and/or palliation of solid tumors in patients. MWA offers several advantages over other ablation technologies such as radiofrequency (RF) and cryoablation including higher temperatures than RF, larger ablation zone volumes, shorter ablation times, and better ablation performance near arteries, which act as heat sinks. Selective delivery of energy to the prescribed tissue volume (i.e. the tumor and its margins) is achieved by means of interstitial placement of a microwave antenna directly into the tumor. Current MWA technology may be employed either laparoscopically or percutaneously, and thus, is considered to be minimally invasive. However, the extent to which MWA is minimally invasive depends on a length and a diameter of the interstitial microwave antenna.

SUMMARY

A balun is provided that includes, but is not limited to, a center conductor, a dielectric material, a tapered wall, a ring, and a prong. The center conductor extends a length of the balun. The dielectric material surrounds the center conductor along the length of the balun. The tapered wall forms a portion of a tube between a first wall and a second wall. The first wall is opposite the second wall. The tapered wall is formed of a conductive material. The portion of the tube forms a slot exposing the dielectric material. The ring connects to the second wall of the tapered wall and is formed of the conductive material. The ring forms a tube surrounding the center conductor and the dielectric material. The prong connects to the ring to extend toward the first wall and is formed of the conductive material. The prong extends over a portion of the dielectric material exposed by the slot.

An antenna system is provided. The antenna system includes, but is not limited to, a coaxial cable, a first dipole arm, and a balun. The coaxial cable includes, but is not limited to, a center conductor extending a length of the coaxial cable, a dielectric material surrounding the center conductor along the length of the coaxial cable, and a conductive shield surrounding the dielectric material along the length of the coaxial cable. The first dipole arm connects to the center conductor. The balun connects between an end of the coaxial cable and the first dipole arm. The balun includes, but is not limited to, a second center conductor, a second dielectric material, a tapered wall, a ring, and a prong. The second center conductor extends a length of the balun and connects to and extends from the center conductor between the center conductor and the first dipole arm. The second dielectric material surrounds the second center conductor along the length of the balun. The tapered wall forms a portion of a tube between a first wall and a second wall, wherein the first wall is opposite the second wall. The first wall is connected to the conductive shield. The tapered wall is formed of a conductive material. The portion of the tube forms a slot exposing the second dielectric material. The ring connects to the second wall of the tapered wall and is formed of the conductive material. The ring forms a tube surrounding the second center conductor and the second dielectric material. The prong connects to the ring to extend toward the first wall and is formed of the conductive material. The prong extends over a portion of the second dielectric material exposed by the slot and forms a second dipole arm.

Other principal features of the disclosed subject matter will become apparent to those skilled in the art upon review of the following drawings, the detailed description, and the appended claims.

BRIEF DESCRIPTION OF THE DRAWINGS

Illustrative embodiments of the disclosed subject matter will hereafter be described referring to the accompanying drawings, wherein like numerals denote like elements.

FIG. 15A depicts the top and right side views of the MWA antenna system of FIGS. 11 and 13 aligned in accordance with an illustrative embodiment.

DETAILED DESCRIPTION

Figure 1:
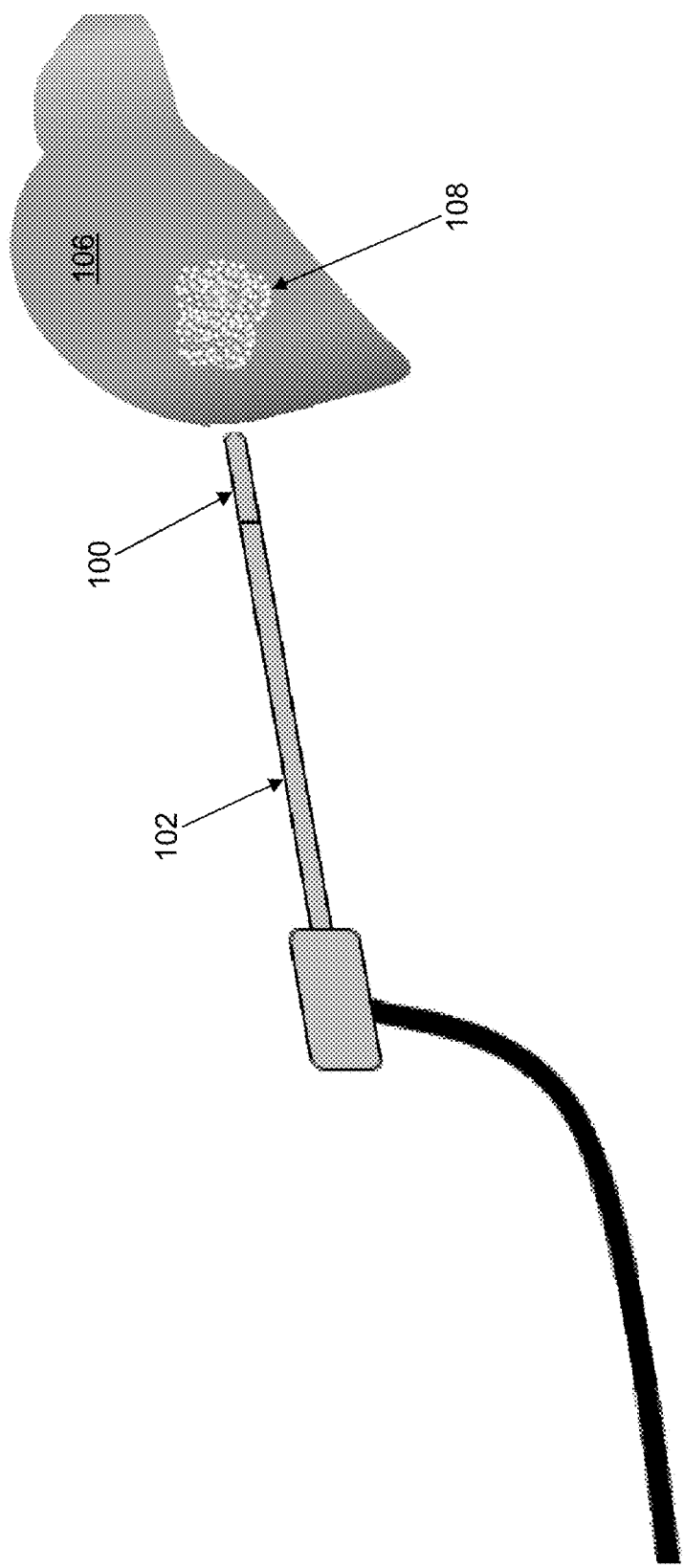
FIG. 1 depicts a microwave ablation (MWA) antenna system in accordance with an illustrative embodiment.

With reference to FIG. 1, a microwave ablation (MWA) antenna 100 is connected to and fed by a coaxial cable 102 that provides electromagnetic energy to antenna 100 at a selected operating frequency $f_0$. MWA can be used to provide thermal therapy for treatment of various types of cancer 108 in various tissue/organs 106. Tissue/organs 106 may include liver, kidney, lung, bone, etc. MWA uses microwave frequency in the range 300 megahertz (MHz) to 300 gigahertz (GHz), though the range from 915 MHz to 2.45 GHz is most commonly used. MWA can be used to elevate the temperature of cancerous tissues to cytotoxic levels (e.g. >50° Celsius (C)) that quickly results in cell death. Electromagnetic waves are introduced into cancerous tissues by inserting antenna 100 interstitially into the tumor or other cancerous tissue.

Typically, interstitial antennas used for MWA are implemented using coaxial cables. When a balanced antenna (antenna 100) is fed by an unbalanced transmission line (coaxial cable 102), unwanted electric currents are excited on the outer conductor of coaxial cable 102. If not properly suppressed, the currents can result in undesired heating and ablation of healthy tissue along the insertion path of antenna 100. A balanced to unbalanced transformer (balun) may be implemented to suppress the currents.

Figure 2:
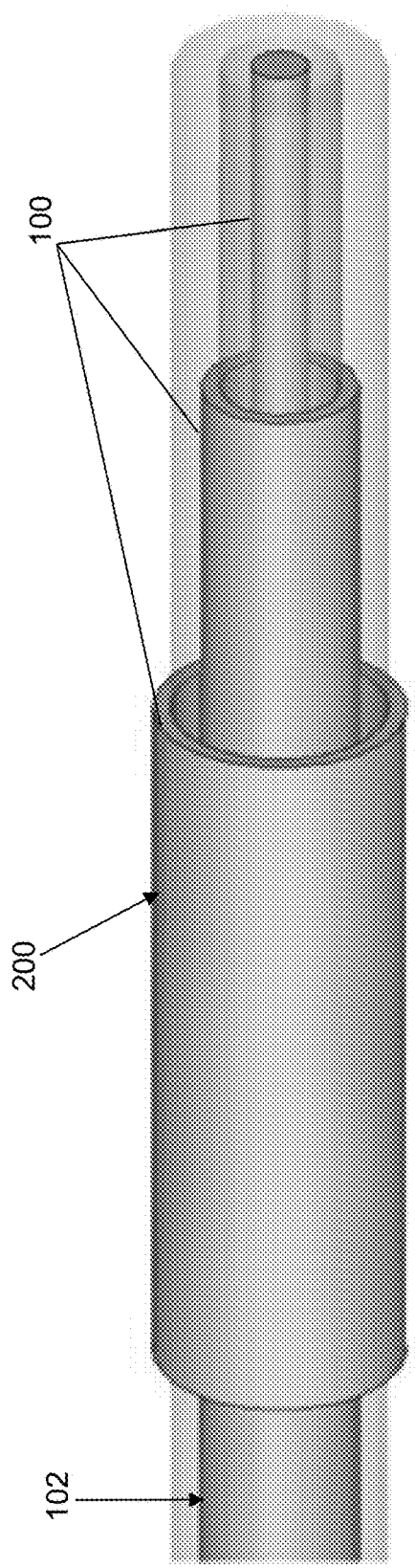
FIG. 2 depicts an MWA antenna system with a prior balun design in accordance with an illustrative embodiment.

With reference to FIG. 2, a widely used solution for choking the undesired outer surface currents for coaxially fed MWA antennas is to use a coaxial balun 200. Coaxial balun 200 includes a cylindrical conductor with a circular cross section that encompasses coaxial cable 102. The cylindrical conductor and the outer conductor of coaxial cable 102 constitute a new coaxial transmission line for the outer surface currents. By properly choosing a length of coaxial balun 200 and terminating its proximal end with a short circuit or an open circuit, a high impedance is presented at its distal end to effectively choke the outer surface currents. However, this coaxial balun 200 increases an overall diameter, and therefore, invasiveness of antenna 100.

Figure 3:
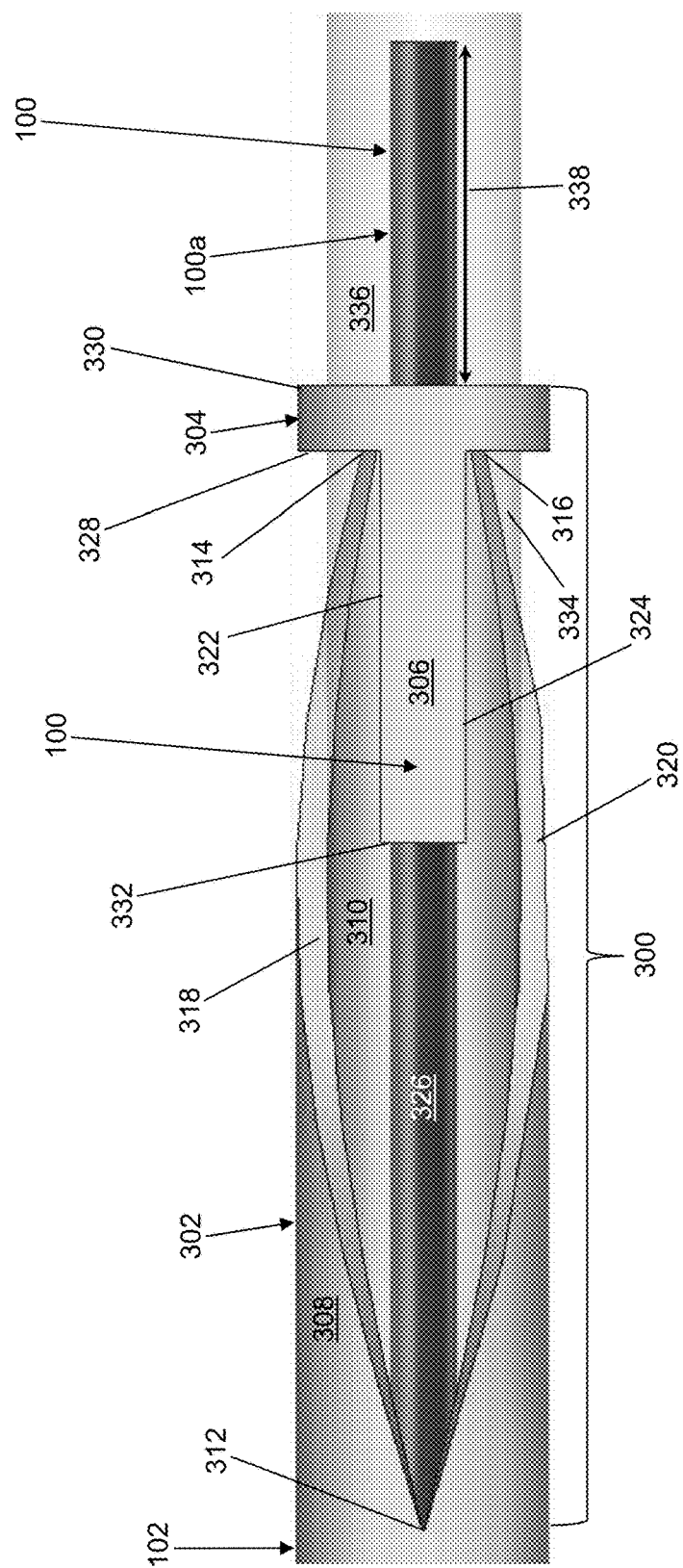
FIG. 3 depicts a top view of an MWA antenna system with a first balun in accordance with an illustrative embodiment.
Figure 4:
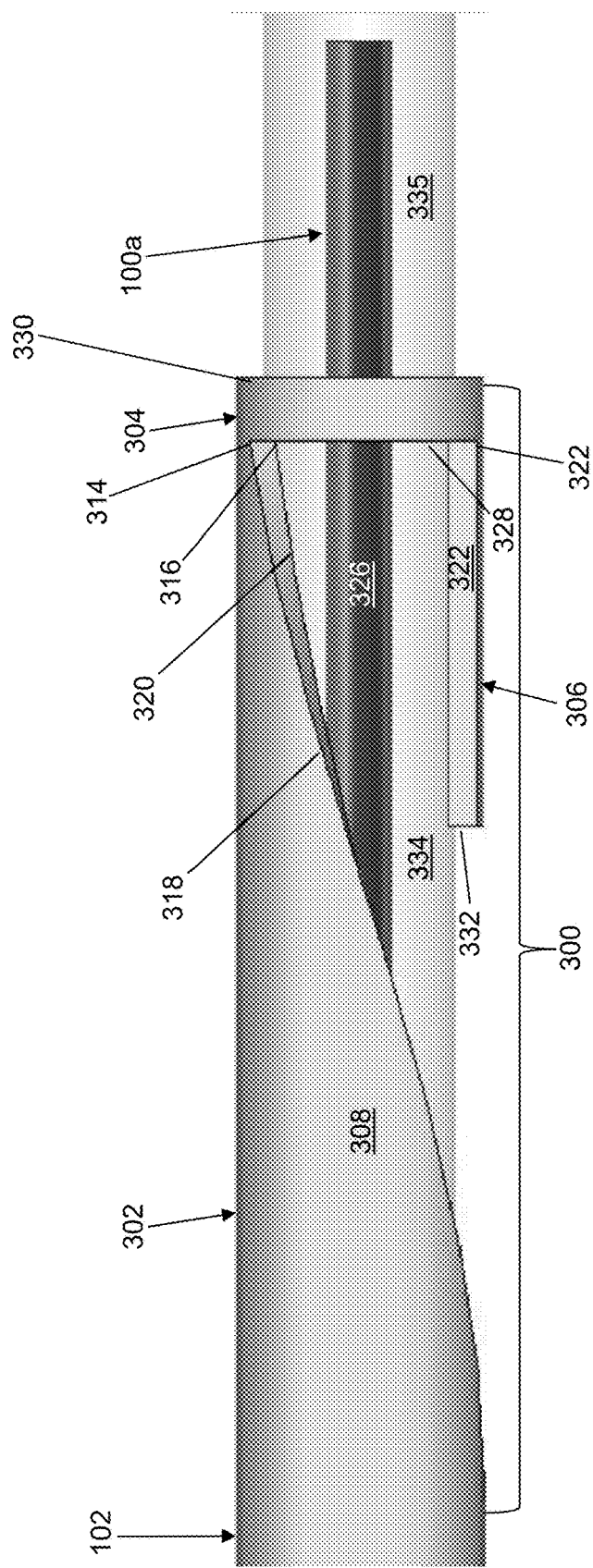
FIG. 4 depicts a right side view of the MWA antenna system of FIG. 3 in accordance with an illustrative embodiment.

With reference to FIG. 3, a top view of antenna 100 with a first balun 300 is shown in accordance with an illustrative embodiment. With reference to FIG. 4, a right side view of antenna 100 with first balun 300 is shown in accordance with an illustrative embodiment. Antenna 100 may be a dipole antenna formed by a first dipole arm 100a and a second dipole arm 306. Second dipole arm 306 may also be referred to herein as a prong. In the illustrative embodiment, second dipole arm 306 has a rectangular shape though other shapes may be used. Because second dipole arm 306 may be integrally formed with the remaining components of first balun 300, second dipole arm 306 is also referred to herein as a portion of first balun 300. First balun 300 is connected between coaxial cable 102 and first dipole arm 100a of antenna 100.

Antenna 100 is formed of a conductive material. As understood by a person of skill in the art, the wavelength of operation, $\lambda_0$, of antenna 100 is defined as $\lambda_0 = c/F_0$, where c is the speed of light in an environment in which antenna 100 is used, such as a body tissue, and $f_0$ is the selected operating frequency. For illustration, $f_0$ may be between 500 MHz and 30 GHz. A cross section of first dipole arm 100a may be circular, square, elliptical, rectangular, etc.

Coaxial cable 102 may include any length of coaxial cable having any characteristic impedance. Coaxial cable 102 may include a center conductor extending a length of coaxial cable 102, a dielectric material surrounding the center conductor along the length of coaxial cable 102, a conductive shield surrounding the dielectric material along the length of coaxial cable 102, and an insulating jacket surrounding the conductive shield along the length of coaxial cable 102 as understood by a person of skill in the art. The center conductor is generally circular and may be formed of a solid conductive material such as copper plated steel wire, silver plated steel wire, silver plated copper wire, silver plated copper clad steel wire, copper wire, copper clad aluminum wire, steel wire, etc. Coaxial cable 102 may have a variety of diameters. The dielectric material may include foamed polyethylene, solid polyethylene, polyethylene foam, polytetrafluoroethylene, air, air space polyethylene, vacuum, alumina, etc. For illustration, the dielectric material may include any low loss dielectric materials having a permittivity relative to a vacuum within the range of 1-10. The conductive shield may be formed of a solid or braided conductive material such as copper, steel, aluminum, silver plated copper, silver plated copper clad steel, etc. The insulating jacket (also known as an outer sheath) can be made from many different insulating materials such as polyvinyl chloride, polytetrafluoroethylene, another plastic material, etc.

Coaxial cable 102 may be rigid, semi-rigid, or flexible. The characteristic impedance may be off the shelf and range between approximately 20 and approximately 125 ohms ($\Omega$) or may be designed to have a selected characteristic impedance within, above, or below this range as understood by a person of skill in the art using various dielectric and conductive materials, diameters, and thicknesses.

First balun 300 may include a tapered wall 302, a ring 304, and second dipole arm 306 that forms a prong connected to and extending from ring 304. First balun 300 is formed of a conductive material. For example, tapered wall 302, ring 304, and second dipole arm 306 may be formed of the same material as the conductive shield of coaxial cable 102. First balun 300 may be created by tapering the conductive shield of a portion of coaxial cable 102 to a wall that connects to ring 304 and removing the material on each side of second dipole arm 306 except where it connects to ring 304 to form a slot and to make a smooth transition from a coaxial line to a parallel wire line.

Figure 5A:
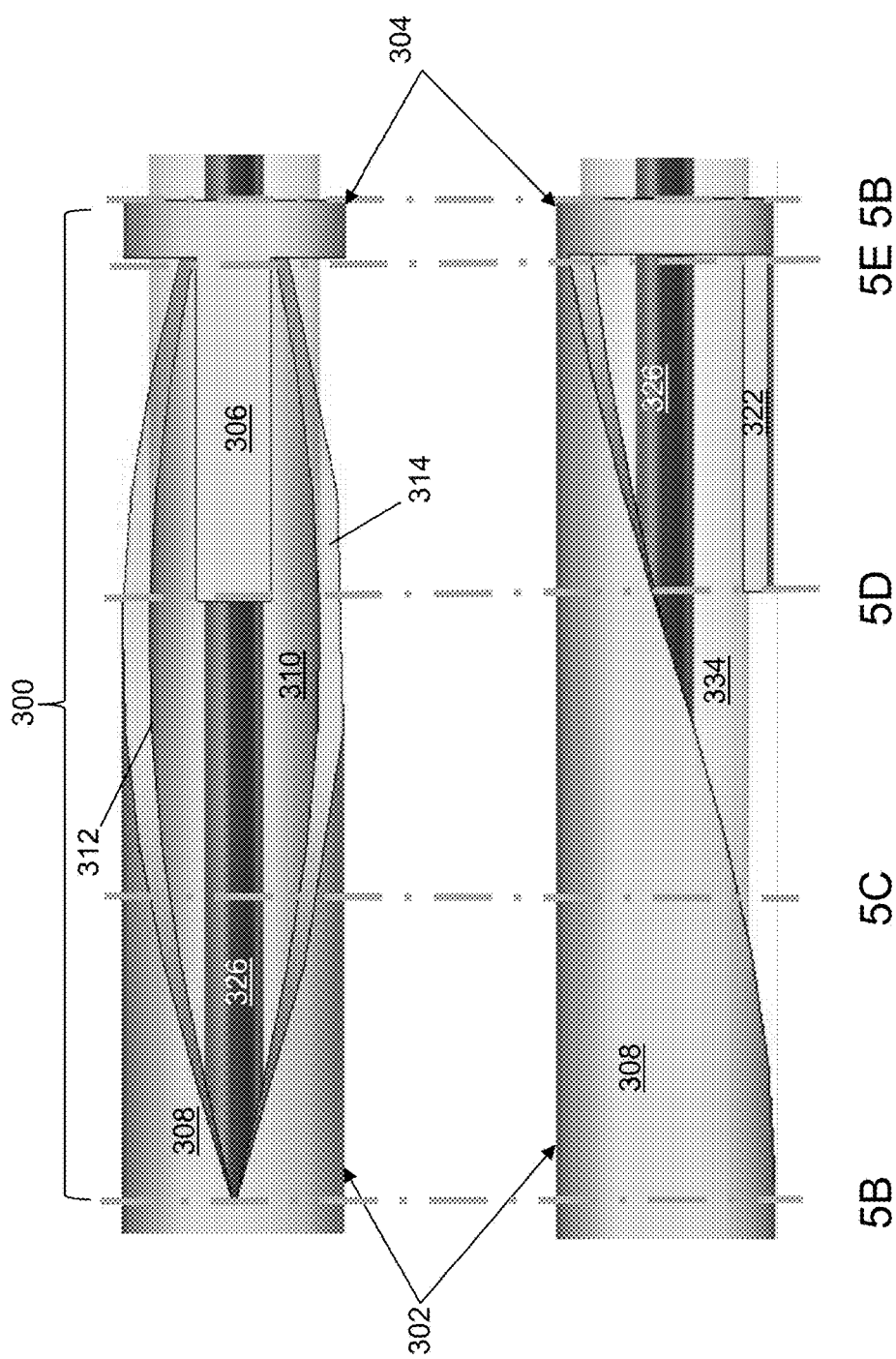
FIG. 5A depicts the top and right side views of the MWA antenna system of FIGS. 3 and 4 aligned in accordance with an illustrative embodiment.
Figure 5C:
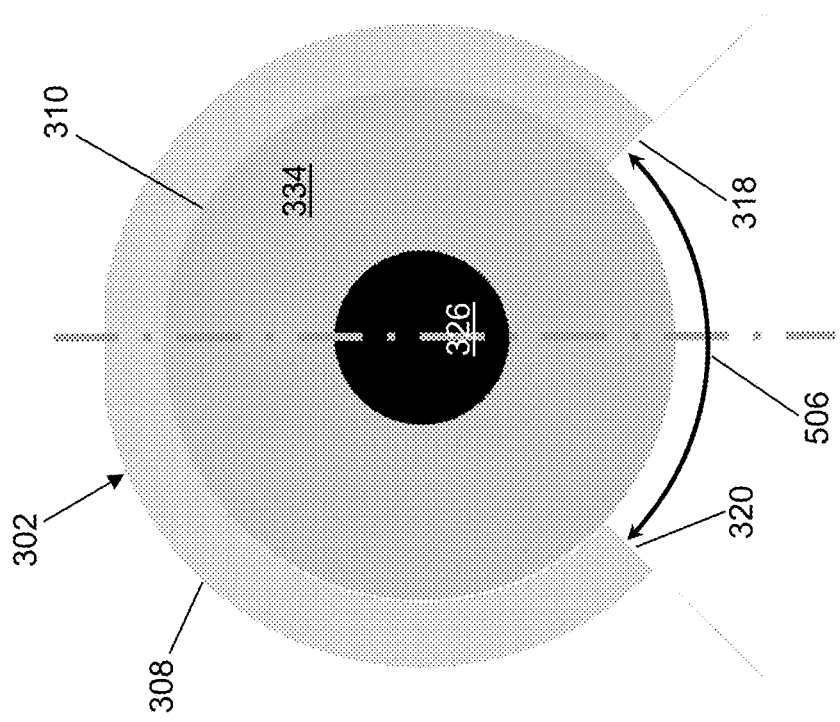
FIGS. 5B-5E depict cross sectional views of the MWA antenna system at cross section locations illustrated in FIG. 5A in accordance with an illustrative embodiment.
Figure 5B:
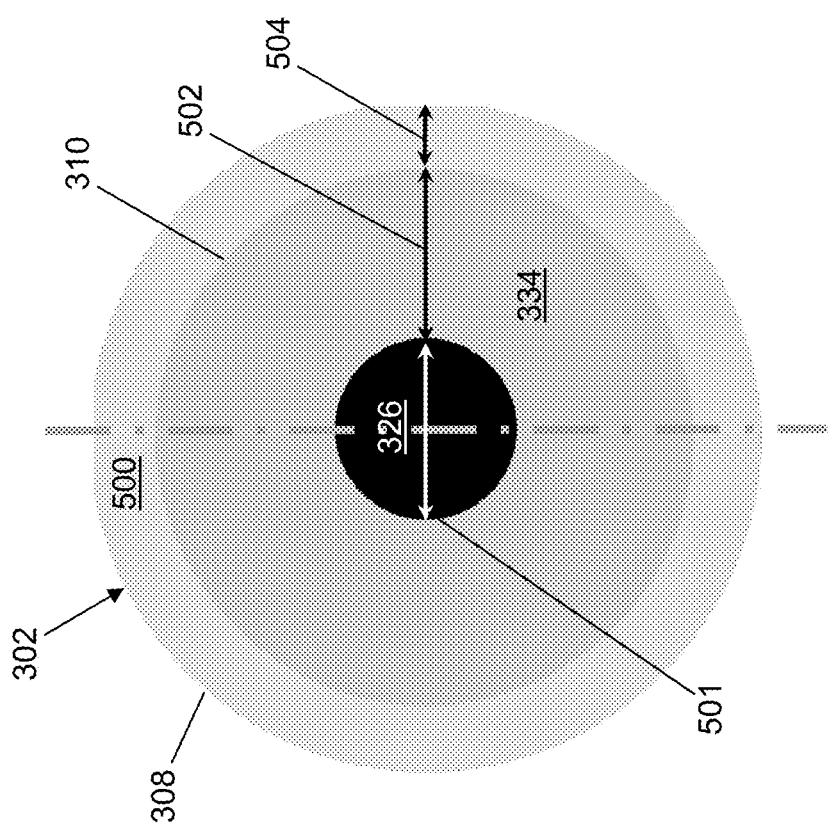
Figure 5E:
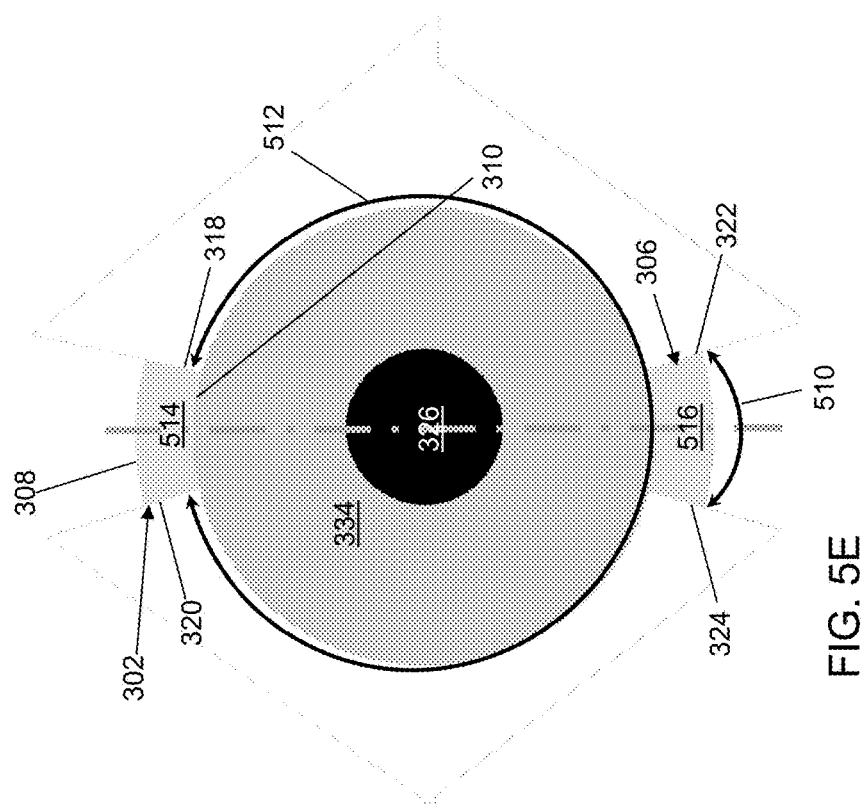

Tapered wall 302 forms a portion of a cylindrical tube between a first wall 500 (shown referring to FIGS. 5B and 6) and a second wall 514 (shown referring to FIG. 5E). First wall 500 is opposite second wall 514. Tapered wall 302 surrounds a balun dielectric material 334. Balun dielectric material 334 may surround a balun center conductor 326. Balun center conductor 326 may be an extension of the center conductor of coaxial cable 102. First dipole arm 100a may be an extension of balun center conductor 326.

The portion of the cylindrical tube forms a slot exposing balun dielectric material 334. Balun dielectric material 334 may be the same material and/or an extension of the dielectric material that surrounds the center conductor of coaxial cable 102. A second dielectric material 336 may further surround first dipole arm 100a. Second dielectric material 336 may be the same material as and/or an extension of balun dielectric material 334.

Tapered wall 302 has an exterior surface 308 and an interior surface 310. The slot formed by tapered wall 302 starts at a slot end point 312 and extends to a first end point 314 and a second end point 316 on either side of second wall 514. A first slot wall 318 extends from slot end point 312 to first end point 314. A second slot wall 320 extends from slot end point 312 to second end point 316.

Second dipole arm 306 extends from a first dipole arm wall 332 that is closest to slot end point 312 to a second dipole arm wall 516 (shown referring to FIG. 5E) that mounts (connects) second dipole arm 306 to ring 304. First dipole arm wall 332 is opposite second dipole arm wall 516. A first arm wall 322 of second dipole arm 306 extends from first dipole arm wall 332 to second dipole arm wall 516. A second arm wall 324 of second dipole arm 306 extends from first dipole arm wall 332 to second dipole arm wall 516. First arm wall 322 and second arm wall 324 are on opposite sides of second dipole arm 306. Second dipole arm 306 forms a semicircular prong.

Ring 304 is connected to second wall 514 of tapered wall 302 and to second dipole arm wall 516 of second dipole arm 306. Ring 304 forms a short cylindrical tube surrounding balun center conductor 326 and balun dielectric material 334. Ring 304 has an inner ring wall 328 and an outer ring wall 330. Second dipole arm 306 is connected to inner ring wall 328 of ring 304, extends towards first wall 500, and is located in the slot created by tapered wall 302. Second dipole arm 306 and first dipole arm 100a extend in opposite directions relative to ring 304. Second wall 514 of tapered wall 302 also connects to inner ring wall 328.

Tapered wall 302 and balun center conductor 326 form a balanced parallel-wire line to feed antenna 100 that includes first dipole arm 100a and second dipole arm 306. Second dipole arm 306 is placed in the slot formed by tapered wall 302 and is connected to tapered wall 302 through ring 304 at second dipole arm wall 516. At its operating frequency, first balun 300 provides balanced currents for antenna 100. As a result, unbalanced currents flowing back on an outer surface of the conductive shield of coaxial cable 102 are minimized.

First balun 300 may be formed by removing a portion of the conductive shield of coaxial cable 102 to form the slot leaving tapered wall 302, second dipole arm 306, and ring 304. For example, a laser may be used to remove the portion of the conductive shield of coaxial cable 102. Thus, first balun 300 may be formed from a portion of coaxial cable 102. As another example, first balun 300 may be etched from a hollow tube of conductive material such as copper and electrically connected to an inner surface of the conductive shield of coaxial cable 102.

A cover (insulating jacket or outer sheath) (not shown) may enclose first dipole arm 100a and first balun 300. The cover may be mounted to allow movement relative to first dipole arm 100a and first balun 300 so that first dipole arm 100a and first balun 300 are protected while inserted into a tissue, but can be exposed once inserted into the tissue.

With reference to FIG. 5A, the top and right side views of FIGS. 3 and 4 are aligned to show cross section locations of first balun 300 shown with reference to FIGS. 5B to 5E. With reference to FIG. 5B, a cross section of first balun 300 taken at slot end point 312 and indicated as 5B in FIG. 5A is shown in accordance with an illustrative embodiment. Balun center conductor 326 has a diameter 501. Balun dielectric material 334 has a dielectric width 502 that surrounds balun center conductor 326. First wall 500 of tapered wall 302 has a conductor width 504 that surrounds balun dielectric material 334 between exterior surface 308 and interior surface 310. A cross section of first balun 300 taken at outer ring wall 330 of ring 304 and also indicated as 5B in FIG. 5A is identical to that taken at slot end point 312 except that wall 500 of tapered wall 302 is replaced with outer ring wall 330 of ring 304.

With reference to FIG. 5C, a cross section of first balun 300 taken at a point as indicated by 5C in FIG. 5A is shown in accordance with an illustrative embodiment. A first arc length 506 defines a slot arc length between first slot wall 318 and second slot wall 320 of tapered wall 302.

Figure 5D:
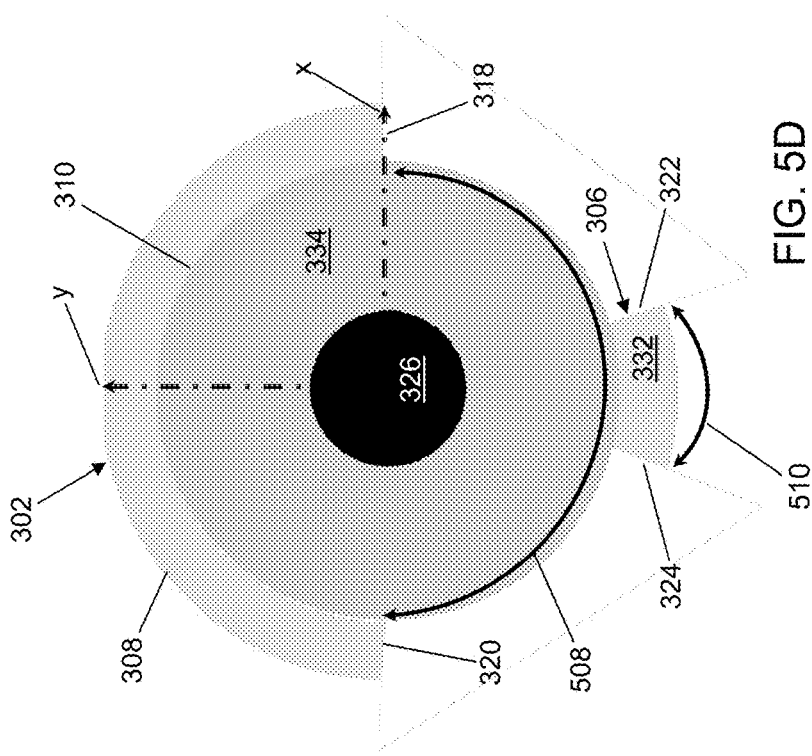

With reference to FIG. 5D, a cross section of first balun 300 taken at first dipole arm wall 332 as indicated by 5D in FIG. 5A is shown in accordance with an illustrative embodiment. A second arc length 508 defines a slot arc length between first slot wall 318 and second slot wall 320 of tapered wall 302 for a cross section taken at first dipole arm wall 332. A prong arc length 510 defines an arc length between first arm wall 322 and second arm wall 324 of second dipole arm 306.

With reference to FIG. 5E, a cross section of first balun 300 taken at second wall 514 of tapered wall 302 and at second dipole arm wall 516 as indicated by 5E in FIG. 5A is shown in accordance with an illustrative embodiment. A third arc length 512 defines a slot arc length between first slot wall 318 and second slot wall 320 at second wall 514 of tapered wall 302.

Figure 6:
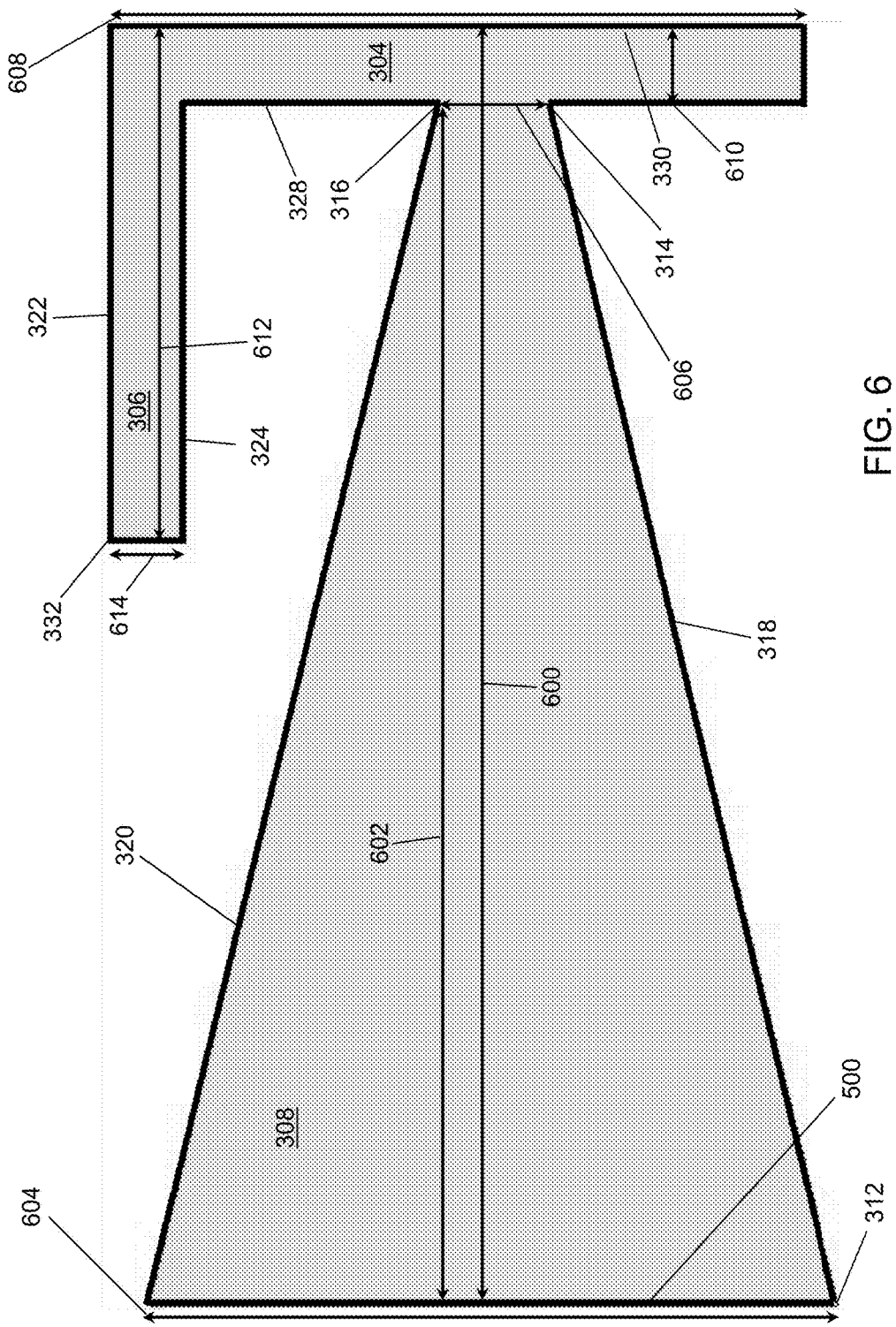
FIG. 6 depicts a top view of the MWA antenna system of FIGS. 3 and 4 unrolled and placed on a flat surface in accordance with an illustrative embodiment.

With reference to FIG. 6, a top view of first balun 300 unrolled and placed on a flat surface is shown in accordance with an illustrative embodiment. A total length 600 of first balun 300 is measured between first wall 500 of tapered wall 302 and outer ring wall 330 of ring 304. A tapered wall length 602 of tapered wall 302 is measured between first wall 500 and second wall 514 of tapered wall 302. A tapered wall circumference 604 defines a circumference of tapered wall 302 at slot end point 312. A tapered wall height 606 is measured between first end point 314 and second end point 316 and defines a length of second wall 514 of tapered wall 302 that mounts to inner ring wall 328 of ring 304. A ring circumference 608 defines a circumference of inner ring wall 328 and outer ring wall 330 of ring 304. A ring width 610 defines a width of ring 304 measured between inner ring wall 328 and outer ring wall 330. A prong length 612 is measured between first dipole arm wall 332 and outer ring wall 330 of ring 304 and includes ring width 610. A prong width 614 defines a width of second dipole arm 306 measured between first arm wall 322 and second arm wall 324. A dipole arm length 338 (shown referring to FIG. 3) is measured as a length of first dipole arm 100a.

In the illustrative embodiment, when flattened, first slot wall 318 and second slot wall 320 have a linear slope. In alternative embodiments, when flattened, first slot wall 318 and second slot wall 320 may have different slopes that may be non-linear. For example, when flattened, first slot wall 318 and second slot wall 320 may form a concave or convex curve between slot end point 312 and first end point and between slot end point 312 and second end point 316, respectively. First slot wall 318 and second slot wall 320 have a complementary shape.

Total length 600 may be selected from a range defined by $$\frac{\lambda_0}{4} \text{ and } \frac{3\lambda_0}{2},$$

where $\lambda_0$ is the wavelength at the operating frequency of the signal carried by balun center conductor 326. Tapered wall height 606, ring width 610, and prong width 614 may each be selected from a range defined by $$\frac{d}{2} \text{ and } 2 \times d,$$

where d is diameter 501 of balun center conductor 326. Tapered wall height 606, ring width 610, and/or prong width 614 may be equal. Prong length 612 and dipole arm length 338 are selected from a range defined by $$\frac{\lambda_1}{4} \text{ and } \frac{\lambda_1}{2},$$

where $\lambda_1$ is an effective wavelength of an operating frequency of a signal carried by balun center conductor 326 in a medium defined by a tissue into which first balun 300 and first dipole arm 100a are at least partially inserted. Tapered wall circumference 604 and ring circumference 608 may be equal to $2\pi r$, where $$r = \frac{d}{2} + d_d + d_c,$$

where $d_d$ equals dielectric width 502, and $d_c$ equals conductor width 504.

For illustration, the parameters of first balun 300 and first dipole arm 100a to achieve localized specific absorption rate (SAR) and heating patterns and a good impedance match between antenna 100 and coaxial cable 102 at 6 GHz were determined using full-wave electromagnetic (EM) simulations of the antennas and simplified thermal simulations. For example, the EM simulations of the antennas were conducted using CST Microwave Studio to design them to operate at 6 GHz in liver tissue. Dielectric properties of liver at room temperature were modeled using a 1-pole Cole Cole model presented for the frequency range from 0 to 8 GHz. Absorption of electromagnetic fields in tissue, calculated from the EM simulations, was scaled for an input power of 20 W to be the heat source in transient thermal simulations in CST Multiphysics Suite. The dimensions were determined as prong length 612 equal to 6.2 millimeters (mm), dipole arm length 338 equal to 7 mm, total length 600 equal to 16 mm, tapered wall height 606, ring width 610, and prong width 614 each equal to 0.5 mm, and tapered wall circumference 604 and ring circumference 608 each equal to $\pi \times 2.2$ mm, the outer circumference of coaxial cable 102. Coaxial cable 102 was selected as 50-Ω UT-085C semi-rigid cable. Copper tubing was used for first balun 300. Polytetrafluoroethylene was used for balun dielectric material 334.

Figure 7:
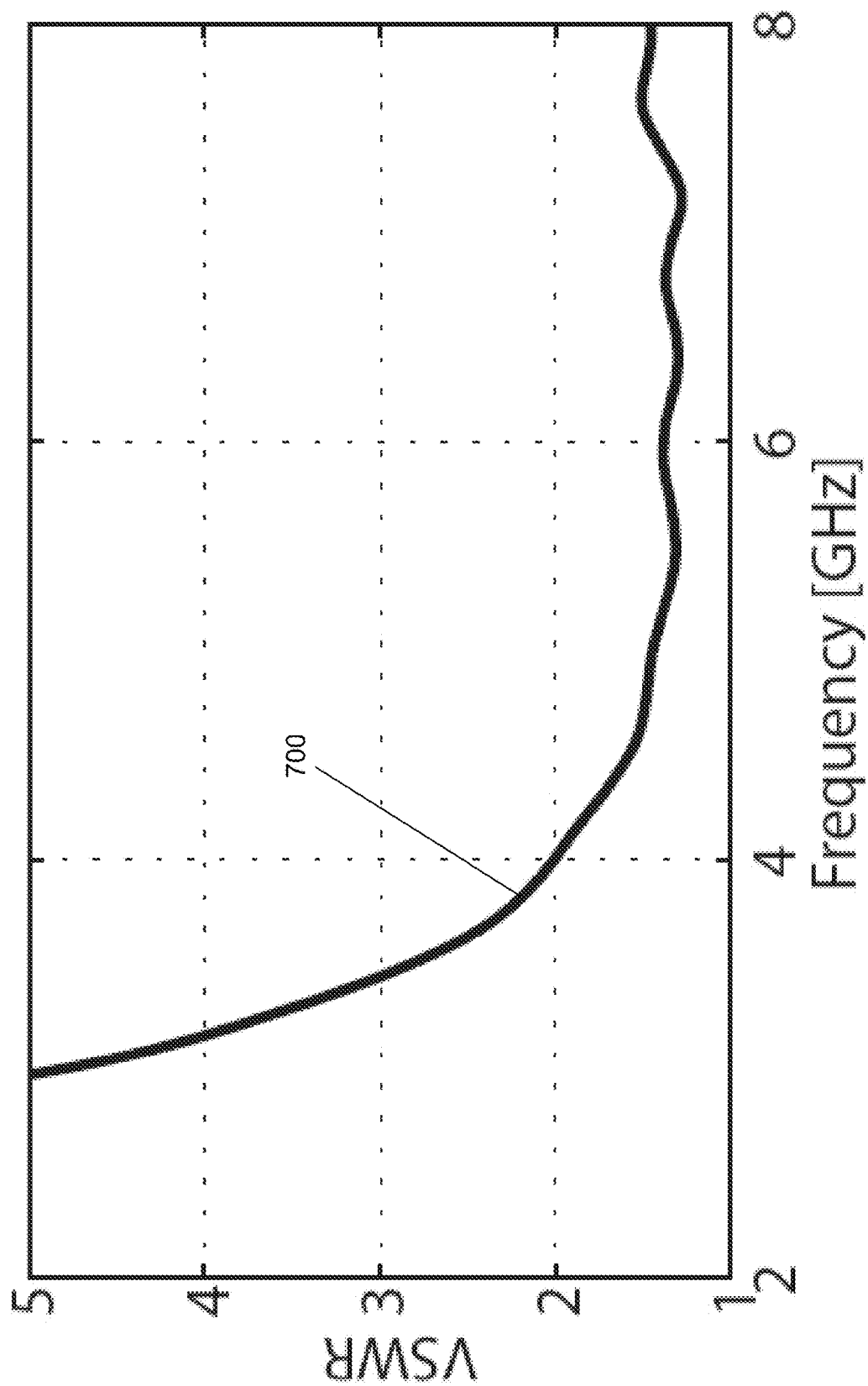
FIG. 7 shows a voltage standing wave ratio as a function of frequency of a simulated MWA antenna system illustrated in FIGS. 3 and 4 in accordance with an illustrative embodiment.

Referring to FIG. 7, a voltage standing wave ratio (VSWR) curve 700 computed from the simulation results is shown. VSWR curve 700 shows a value less than two from four GHz to over eight GHz.

Figure 8:
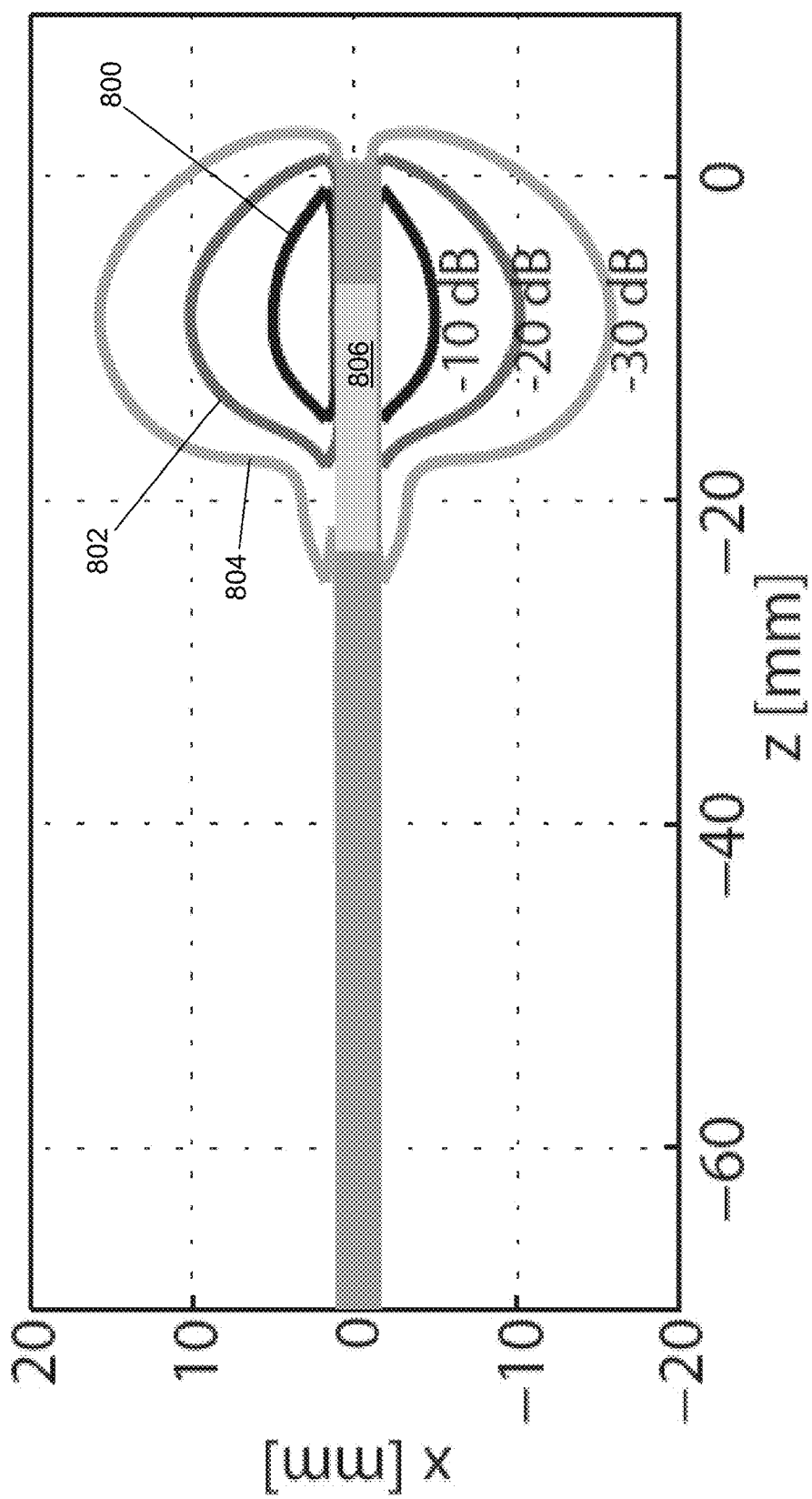
FIG. 8 shows a normalized specific absorption rate (SAR) pattern of the MWA antenna system of FIGS. 3 and 4 in the x-z plane in accordance with an illustrative embodiment.
Figure 9:
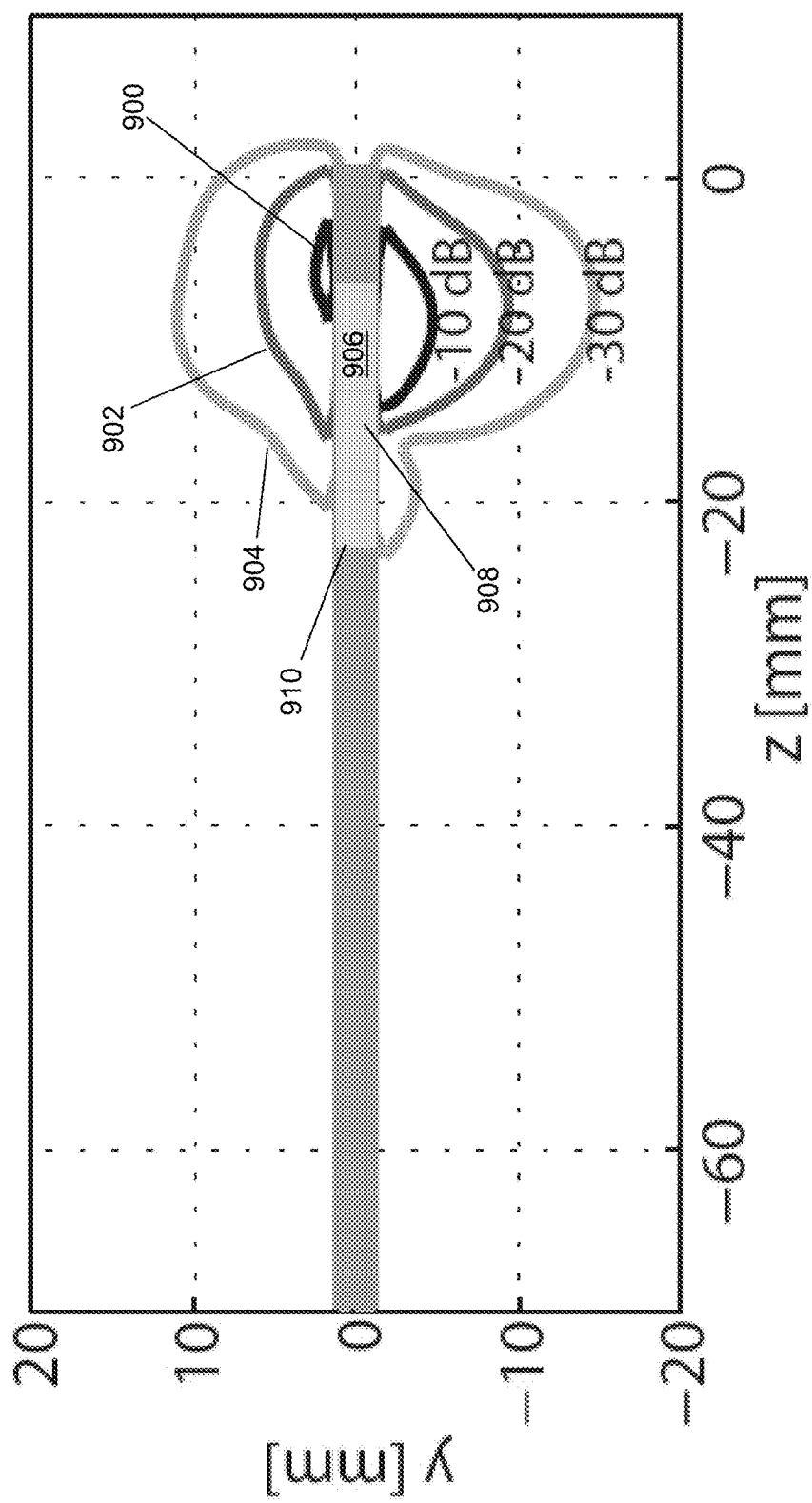
FIG. 9 shows a normalized SAR pattern of the MWA antenna system of FIGS. 3 and 4 in the y-z plane in accordance with an illustrative embodiment.

Referring to FIGS. 8 and 9, a normalized specific absorption rate (SAR) pattern of antenna 100 with first balun 300 is shown in the x-z and y-z planes, respectively, where z is along an axis of balun center conductor 326. The x-y planes define the cross sections of first balun 300 with the x-axis and the y-axis as indicated in FIG. 5D. Referring to FIG. 8, a −10 decibel (dB) curve 800 shows a SAR level reduced by 10 dB compared to a maximum SAR level. A −20 dB curve 802 shows a SAR level reduced by 20 dB compared to the maximum SAR level. A −30 dB curve 804 shows a SAR level reduced by 30 dB compared to the maximum SAR level. A region 806 indicates a location of first balun 300 for reference.

Referring to FIG. 9, a −10 dB curve 900 shows a SAR level reduced by 10 dB compared to the maximum SAR level. A −20 dB curve 902 shows a SAR level reduced by 20 dB compared to the maximum SAR level. A −30 dB curve 904 shows a SAR level reduced by 30 dB compared to the maximum SAR level. A region 906 indicates a location of first balun 300 for reference. A proximal end 908 of second dipole arm 306 shows a reduction of approximately 20 dB in SAR level. A proximal end 910 of first balun 300 shows a reduction of approximately 30 dB in SAR level. The results indicate that the outer surface currents are effectively suppressed using first balun 300, resulting in a compact SAR pattern with minimal tails along the shaft of coaxial cable 102.

Figure 10:
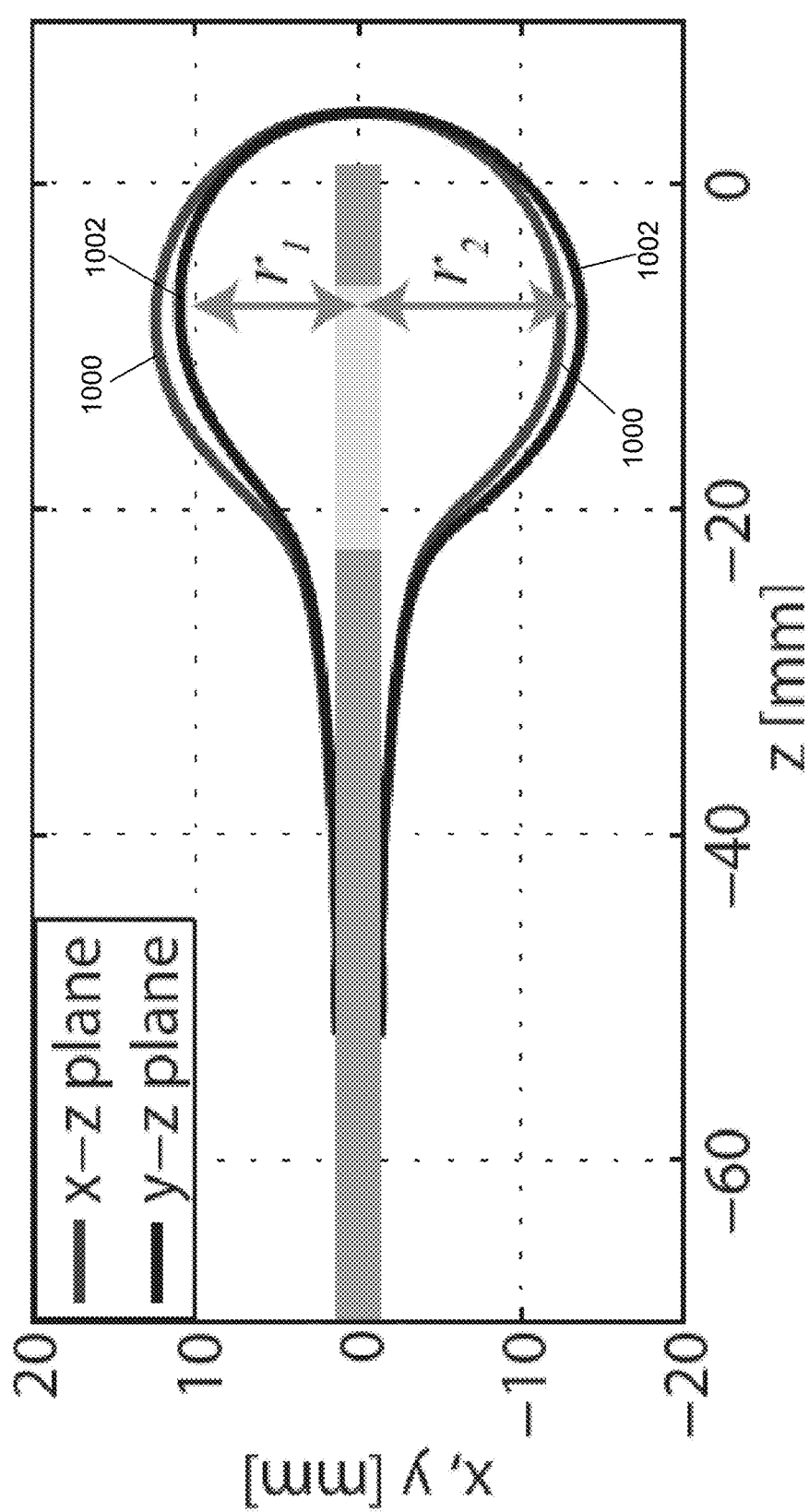
FIG. 10 shows a 50° Celsius contour after 5 minutes of ablation using the MWA antenna system of FIGS. 3 and 4 with 20 Watts of input power in the x-z and y-z planes in accordance with an illustrative embodiment.

An asymmetric heating pattern results due to a lack of symmetry in the placement of second dipole arm 306 that is connected to tapered wall 302 in the y-z plane. As a result, the electromagnetic radiation is stronger on the lower side, where second dipole arm 306 is located, compared to an upper side where tapered wall 302 is located. Referring to FIG. 10, a simulated 50° C. contour, used to predict a boundary of an ablation zone, is shown in the x-z and the y-z planes at the end of a five minute ablation using an input power of 20 Watts (W). An x-z ablation zone 1000 is symmetrical in the x-z plane. A y-z ablation zone 1002 is slightly asymmetrical in the y-z plane, as a result of the corresponding SAR pattern in these two cut planes. However, maximum lateral dimensions of the ablation zone in the two cut planes are the same and equal to 24 mm. In the y-z plane, the maximum lateral radius of the ablation zone is 10.75 mm for the upper side ($r_1$) and 13.25 mm for the lower side ($r_2$). While this degree of asymmetry is not significant, further modification of the antenna design to create a more asymmetric ablation zone can be implemented such as tilting first dipole arm 100a and second dipole arm 306 toward a lower half of the y-z plane or deploying a hemi-cylindrical metallic reflector to prevent EM radiation on the upper half of the y-z plane. Additionally, such asymmetrically enhanced heating may be desirable in certain clinical scenarios where tumors are highly asymmetric or where an antenna has to heat a tumor from a peripheral position because the central region of the tumor is inaccessible (e.g. blockage by other vital organs).

Figure 11:
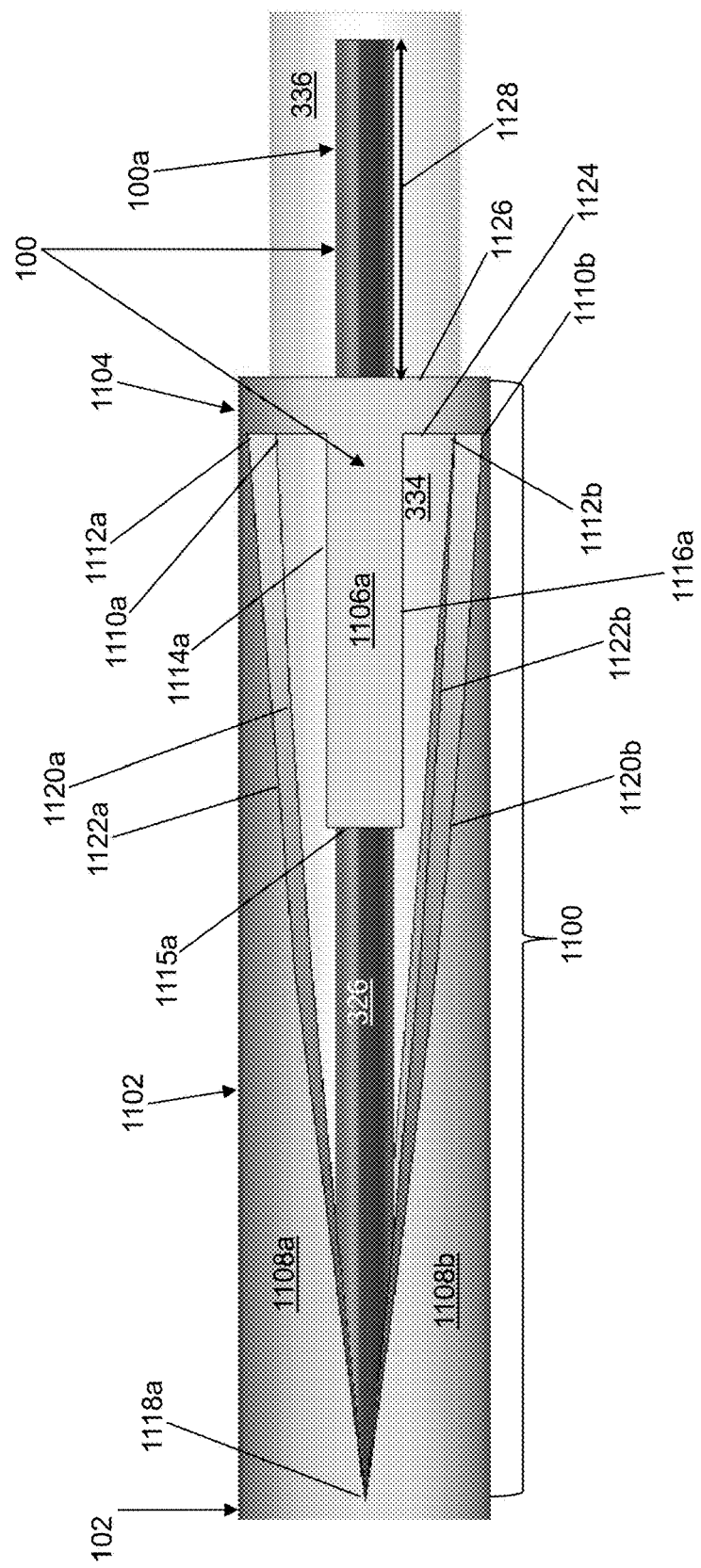
FIG. 11 depicts a top view of an MWA antenna system with a second balun in accordance with an illustrative embodiment.
Figure 12:
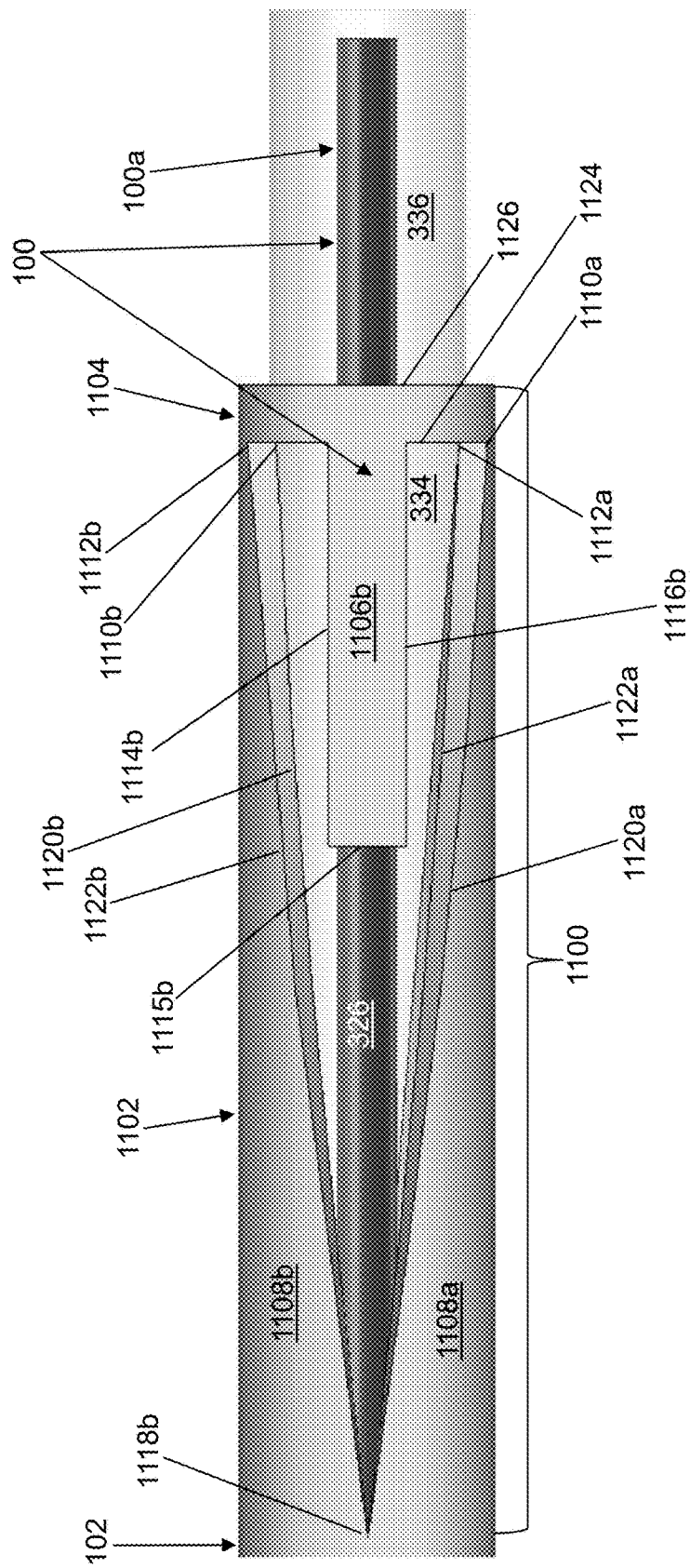
FIG. 12 depicts a bottom view of the MWA antenna system of FIG. 11 in accordance with an illustrative embodiment.
Figure 13:
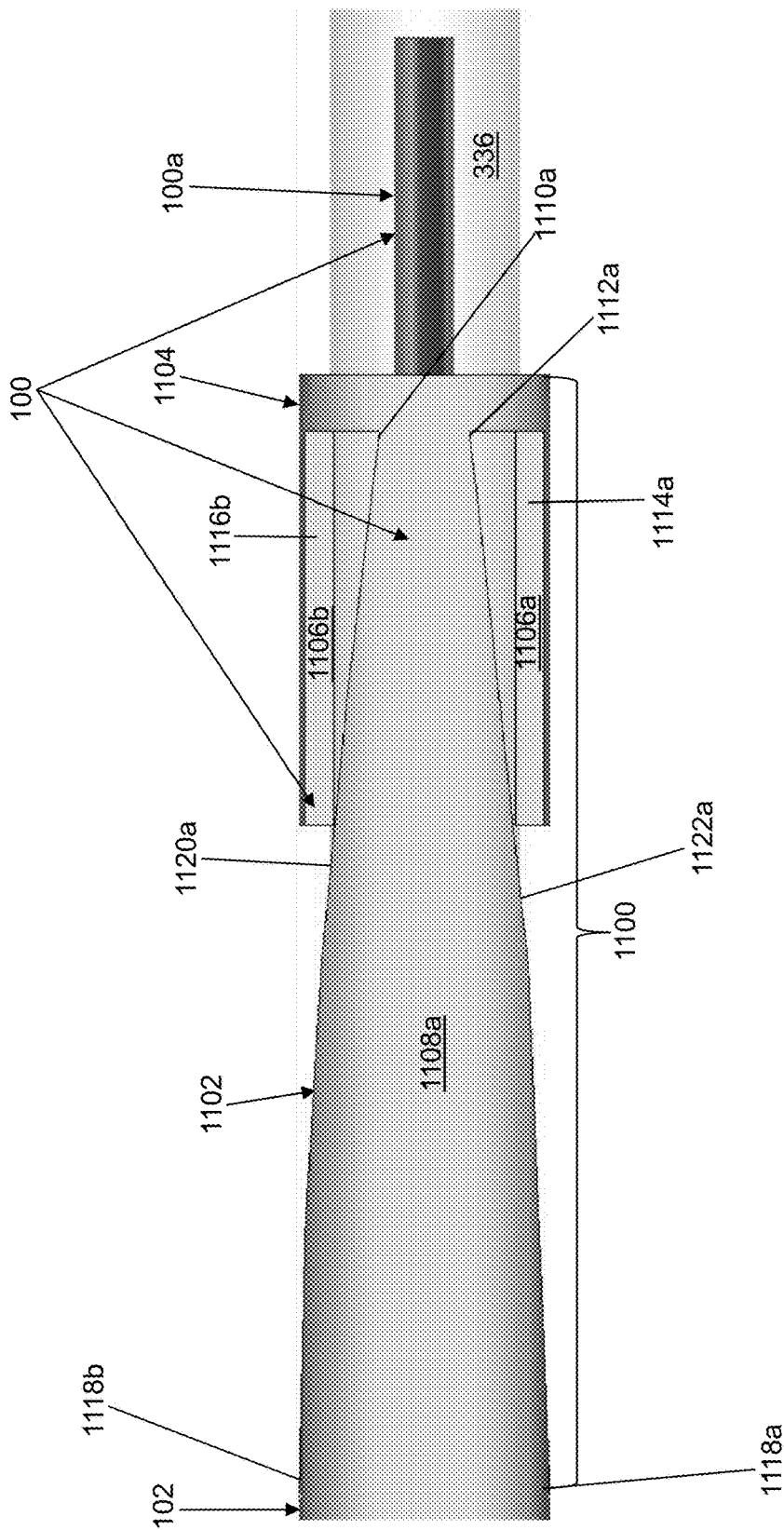
FIG. 13 depicts a right side view of the MWA antenna system of FIG. 11 in accordance with an illustrative embodiment.
Figure 14:
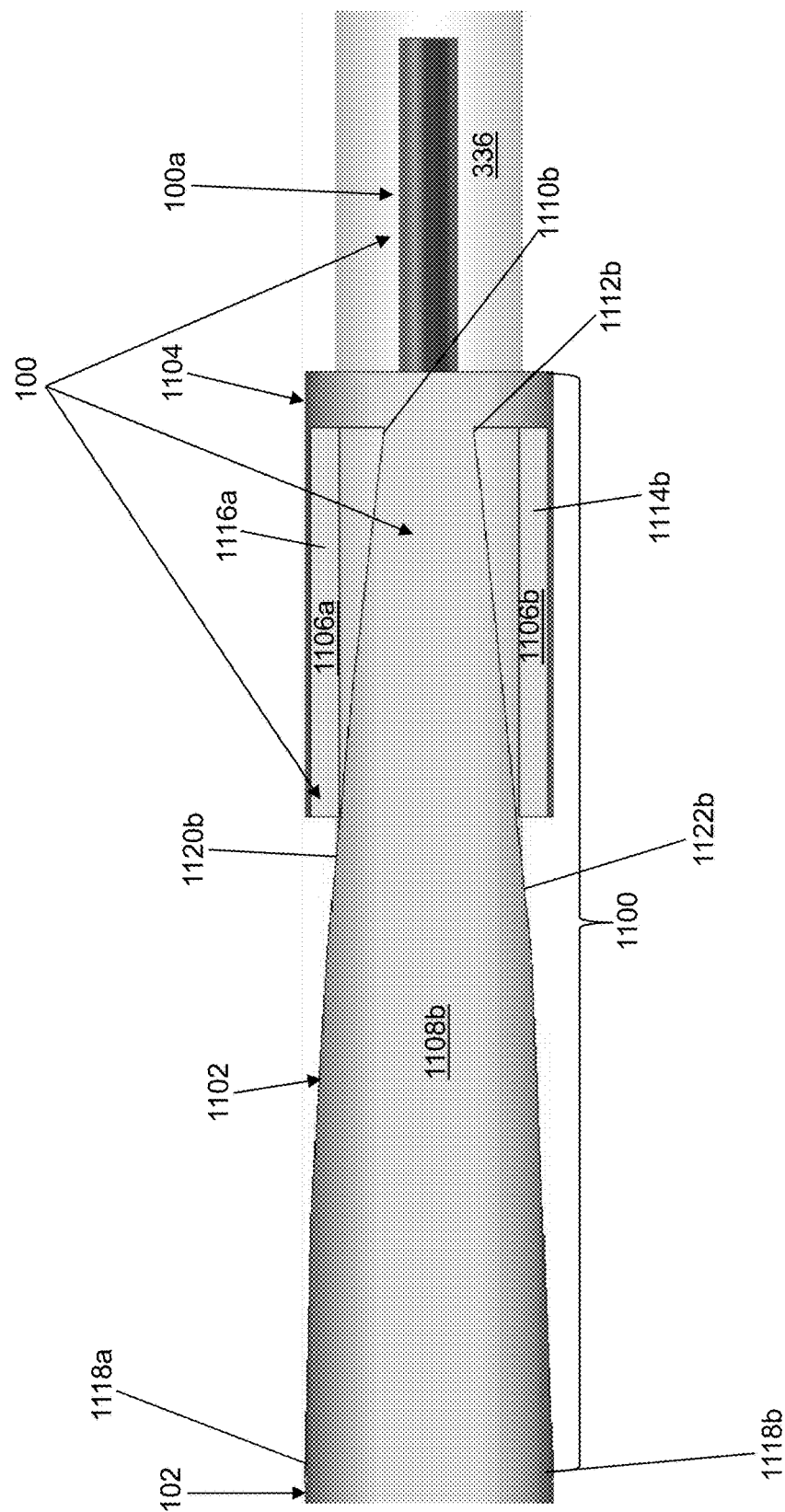
FIG. 14 depicts a left side view of the MWA antenna system of FIG. 11 in accordance with an illustrative embodiment.

With reference to FIG. 11, a top view of first dipole arm 100a with a second balun 1100 is shown in accordance with an illustrative embodiment. With reference to FIG. 12, a bottom view of first dipole arm 100a with second balun 1100 is shown in accordance with an illustrative embodiment. With reference to FIG. 13, a right side view of first dipole arm 100a with second balun 1100 is shown in accordance with an illustrative embodiment. With reference to FIG. 14, a left side view of first dipole arm 100a with second balun 1100 is shown in accordance with an illustrative embodiment. Antenna 100 may be a dipole antenna formed by first dipole arm 100a, a second dipole arm 1106a, and a third dipole arm 1106b. Second balun 1100 is similar to first balun 300 except that two slots are formed instead of one forming a symmetric structure with two slots opposite each other and with second dipole arm 1106a and third dipole arm 1106b opposite each other circumferentially around second balun 1100.

Second dipole arm 1106a and third dipole arm 1106b may each be referred to herein as a prong. Second dipole arm 1106a and third dipole arm 1106b are connected to a ring 1104 to form one arm of antenna 100 that again forms a dipole. Again, first dipole arm 100a is the second arm of the dipole.

In the illustrative embodiment, second dipole arm 1106a and third dipole arm 1106b have a rectangular shape though other shapes may be used. Because second dipole arm 1106a and third dipole arm 1106b may be integrally formed with the remaining components of second balun 1100, second dipole arm 1106a and third dipole arm 1106b are also referred to herein as portions of second balun 1100. Second balun 1100 is connected between coaxial cable 102 and first dipole arm 100a of antenna 100.

Second balun 1100 may include a tapered wall 1102, ring 1104, second dipole arm 1106a, and third dipole arm 1106b that form prongs connected to and extending from ring 1104. Second balun 1100 is formed of a conductive material. For example, tapered wall 1102, ring 1104, second dipole arm 1106a, and third dipole arm 1106b may be formed of the same material as the conductive shield of coaxial cable 102. Second balun 1100 may be created by tapering the conductive shield of a portion of coaxial cable 102 to form two walls that connect to ring 1104 and removing the material on each side of second dipole arm 1106a and of third dipole arm 1106b except where each connects to ring 1104 to form two slots and to make a smooth transition from a coaxial line to a parallel wire line.

Tapered wall 1102 includes a first tapered wall 1108a and a second tapered wall 1108b. First tapered wall 1108a and second tapered wall 1108b are similar to tapered wall 302. First tapered wall 1108a and second tapered wall 1108b form two portions of a cylindrical tube between a first wall 1506 (shown referring to FIGS. 15B and 16) and a second wall 1520a and a third wall 1520b, respectively (shown referring to FIG. 15E). First wall 1506 is opposite second wall 1520a and third wall 1520b. First tapered wall 1108a and second tapered wall 1108b surround balun dielectric material 334, which again surrounds balun center conductor 326. The portion of the cylindrical tube forms two slots exposing balun dielectric material 334.

Figure 15B:
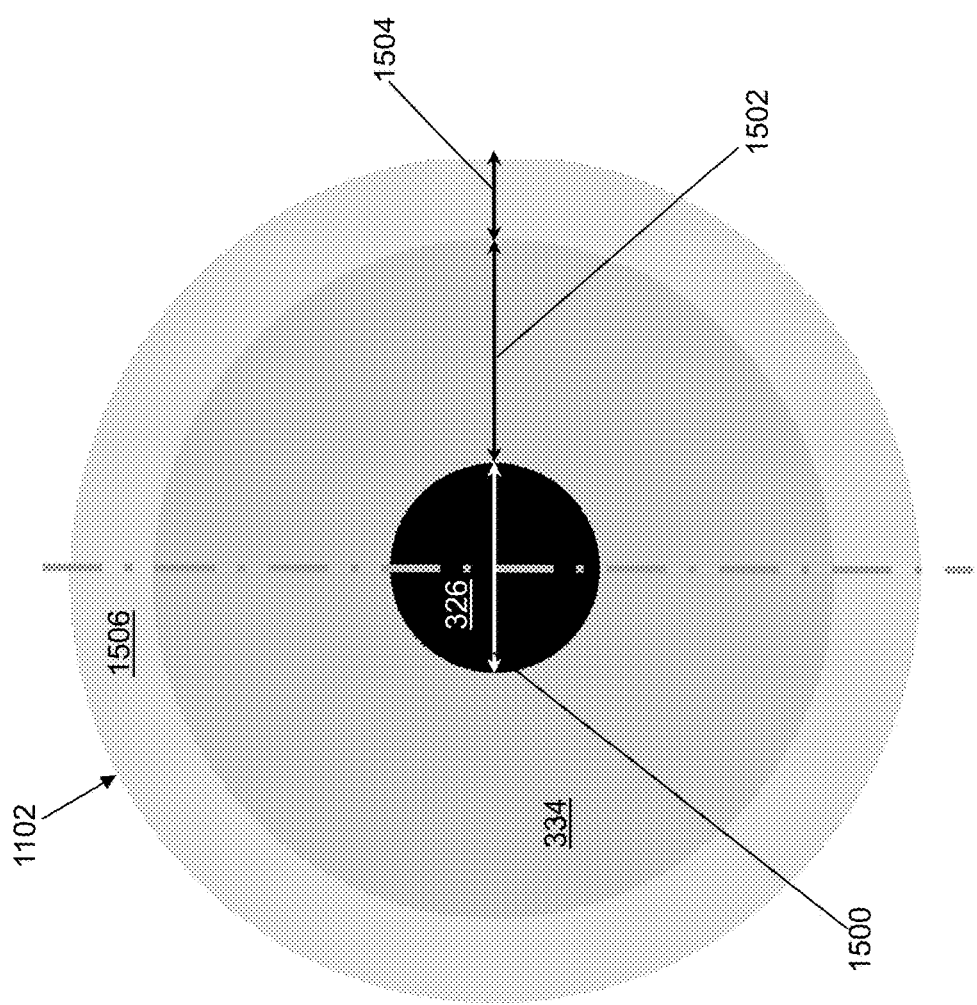
FIGS. 15B-15E depict cross sectional views of the MWA antenna system at cross section locations illustrated in FIG. 15A in accordance with an illustrative embodiment.
Figure 15C:
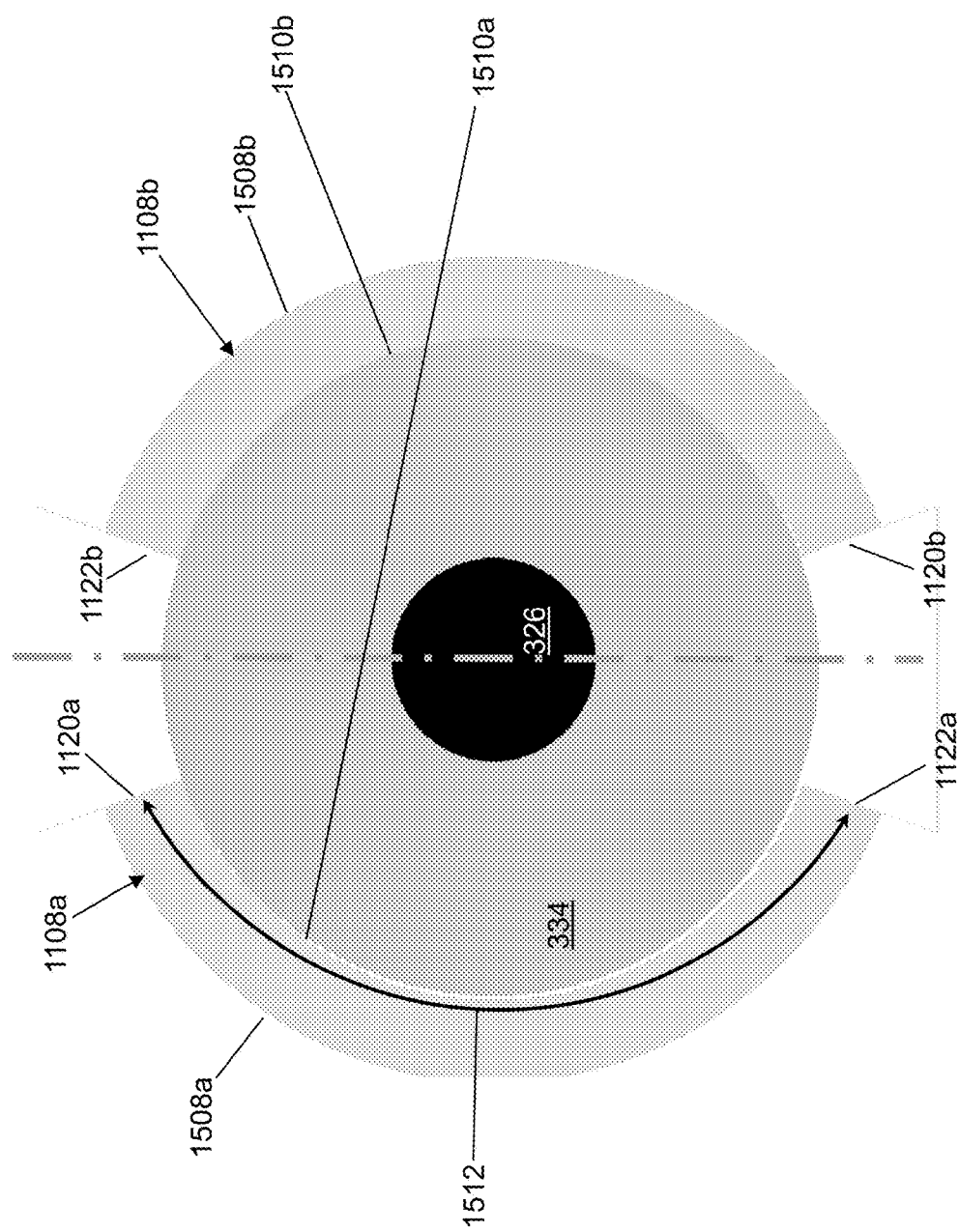

First tapered wall 1108a has an exterior surface 1508a (shown referring to FIG. 15C) and an interior surface 1510a (shown referring to FIG. 15C). First tapered wall 1108a starts at a first slot end point 1118a on a first side and a second slot end point 1118b on a second side. A first slot wall 1120a of first tapered wall 1108a extends from second slot end point 1118b to first end point 1110a. A second slot wall 1122a of first tapered wall 1108a extends from first slot end point 1118a to second end point 1112a.

Second tapered wall 1108b has an exterior surface 1508b (shown referring to FIG. 15C) and an interior surface 1510b (shown referring to FIG. 15C). Second tapered wall 1108b starts at first slot end point 1118a on a first side and second slot end point 1118b on a second side. A third slot wall 1120b of second tapered wall 1108b extends from first slot end point 1118a to third end point 1110b. A fourth slot wall 1122b of second tapered wall 1108b extends from second slot end point 1118b to fourth end point 1112b.

Figure 15D:
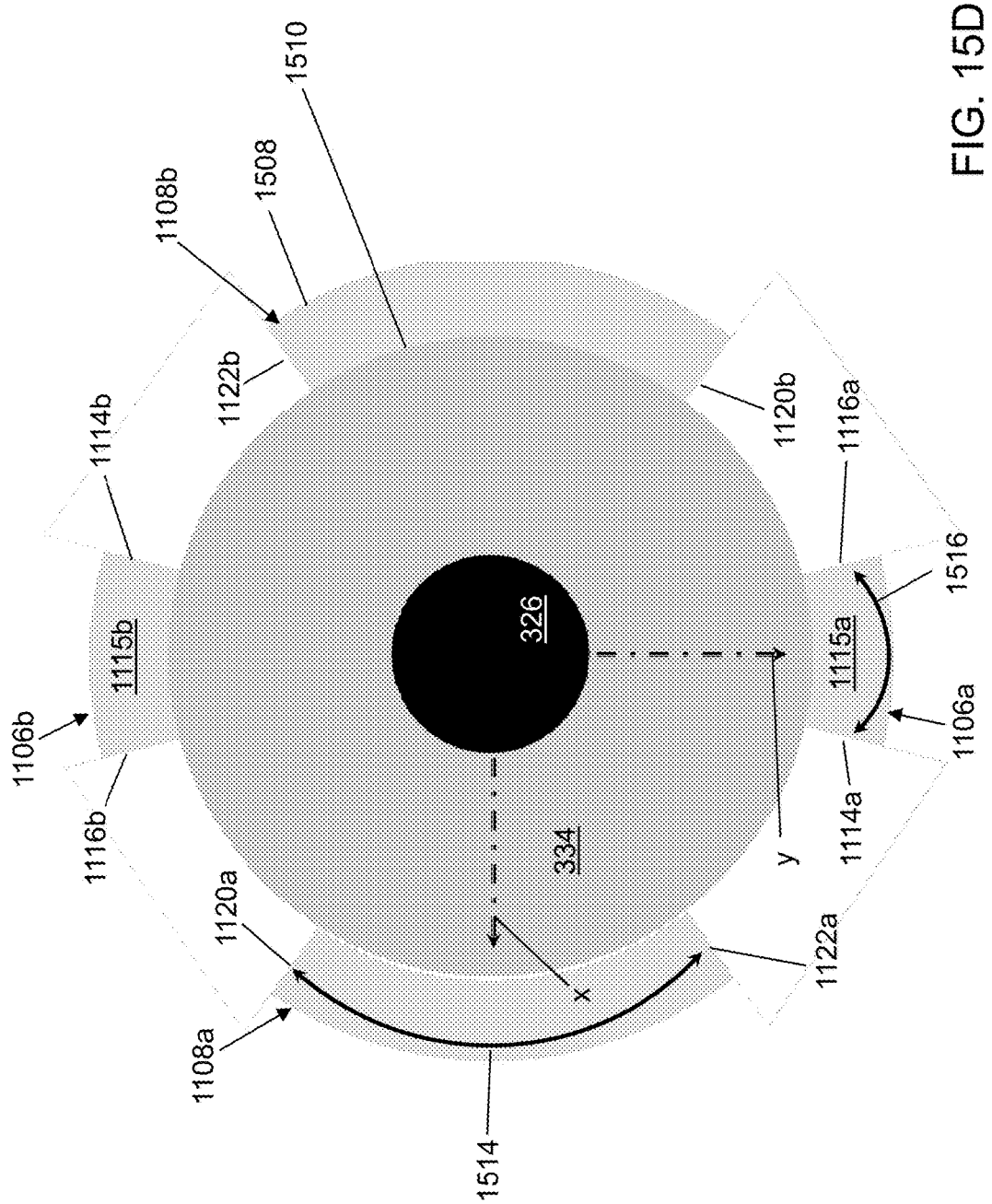
Figure 15E:
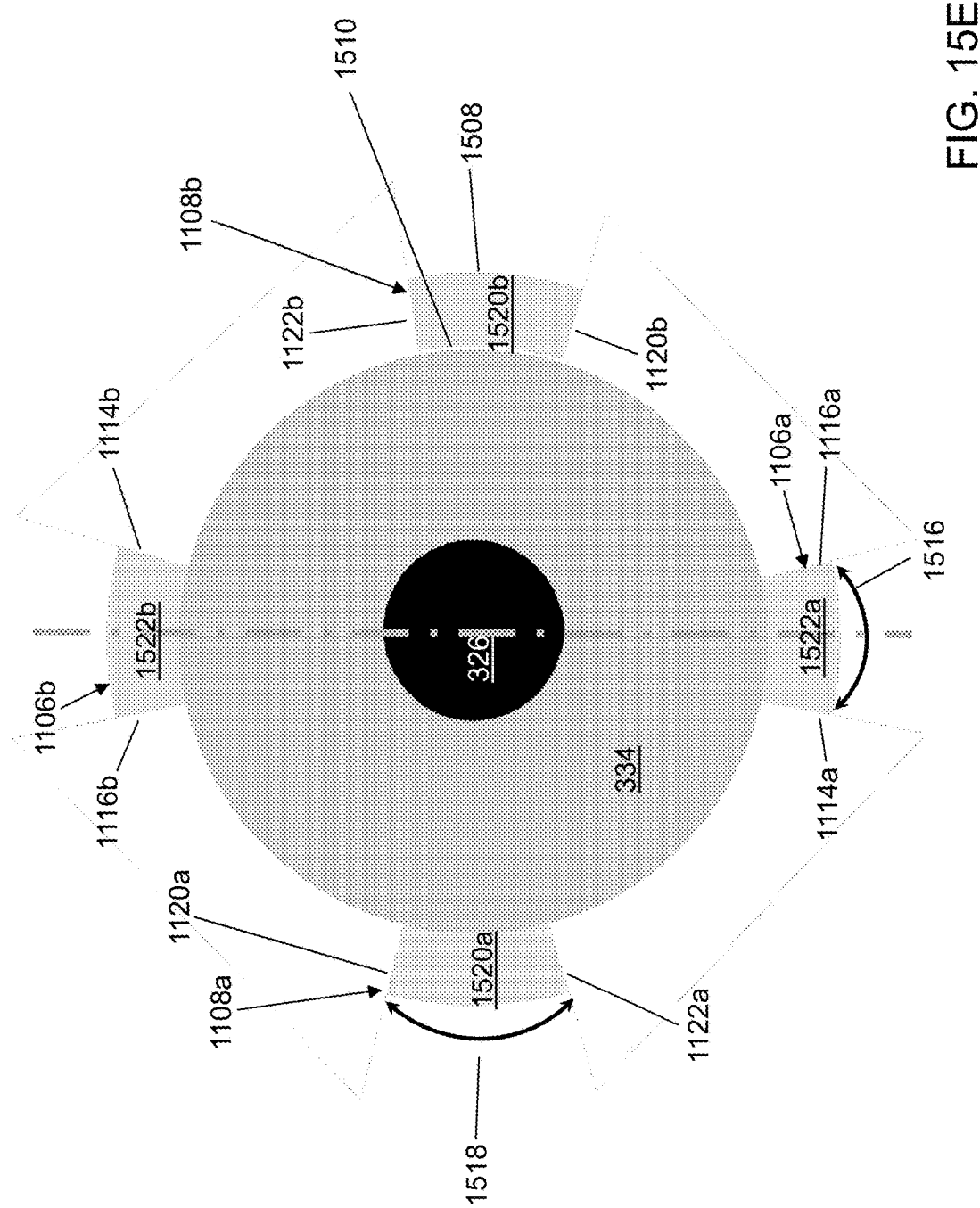

Second dipole arm 1106a extends from a first dipole arm wall 1115a that is closest to first slot end point 1118a to a second dipole arm wall 1522a (shown referring to FIG. 15E). First dipole arm wall 1115a is opposite second dipole arm wall 1522a. Second dipole arm wall 1522a mounts to ring 1104 between a first arm wall 1114a and a second arm wall 1116a. Second dipole arm 1106a forms a semicircular prong.

Third dipole arm 1106b extends from a third dipole arm wall 1115b that is closest to second slot end point 1118b to a third dipole arm wall 1522b (shown referring to FIG. 15E). Third dipole arm wall 1115b is opposite third dipole arm wall 1522b. Third dipole arm wall 1522b mounts to ring 1104 between a third arm wall 1114b and a fourth arm wall 1116b. Third dipole arm 1106b forms a semicircular prong.

Ring 1104 is similar to ring 304. Ring 1104 is connected to second wall 1520a of first tapered wall 1108a, to third wall 1520b of second tapered wall 1108b, to second dipole arm wall 1522a of second dipole arm 1106a, and to third dipole arm wall 1522b of third dipole arm 1106b. Ring 1104 forms a short cylindrical tube surrounding balun center conductor 326 and balun dielectric material 334. Ring 1104 has an inner ring wall 1124 and an outer ring wall 1126. Second dipole arm 1106a and third dipole arm 1106b are connected to inner ring wall 328 of ring 1104, extend towards first wall 1506, and are located in slots created by first tapered wall 1108a and second tapered wall 1108b, respectively. Second dipole arm 1106a and third dipole arm 1106b extend in a direction opposite to first dipole arm 100a relative to ring 1104.

First tapered wall 1108a, second tapered wall 1108b, and balun center conductor 326 form a balanced parallel-wire line to feed antenna 100 that includes first dipole arm 100a, second dipole arm 1106a, and third dipole arm 1106b. Second dipole arm 1106a and third dipole arm 1106b are placed in the slots formed by first tapered wall 1108a and second tapered wall 1108b and are connected to tapered wall 302 through ring 1104 at second dipole arm wall 1522a and at third dipole arm wall 1522b, respectively. At its operating frequency, second balun 1100 provides balanced currents for antenna 100. As a result, unbalanced currents flowing back on an outer surface of the conductive shield of coaxial cable 102 are minimized.

Second balun 1100 may be formed by removing a portion of the conductive shield of coaxial cable 102 to form the two slots, second dipole arm 1106a, and third dipole arm 1106b. For example, a laser may be used to remove the portion of the conductive shield of coaxial cable 102. As another example, second balun 1100 may be etched from a hollow tube of conductive material such as copper and electrically connected to an inner surface of the conductive shield of coaxial cable 102.

A cover (not shown) may enclose first dipole arm 100a and second balun 1100. The cover may be mounted to allow movement relative to first dipole arm 100a and second balun 1100 so that first dipole arm 100a and second balun 1100 are protected while inserted into a tissue, but can be exposed once inserted into the tissue.

With reference to FIG. 15A, the top and right side views of FIGS. 11 and 13 are aligned to show cross section locations of second balun 1100 shown with reference to FIGS. 15B to 15E. With reference to FIG. 15B, a cross section of second balun 1100 taken at first slot end point 1118a and at second slot end point 1118b and indicated as 15B in FIG. 15A is shown in accordance with an illustrative embodiment. Balun center conductor 326 has a diameter 1500. Balun dielectric material 334 has a dielectric width 1502 that surrounds balun center conductor 326. Tapered wall 1102 has a conductor width 1504 that surrounds balun dielectric material 334. A cross section of second balun 1100 taken at outer ring wall 1126 of ring 1104 is identical to that taken at first slot end point 1118a and at second slot end point 1118b. A cross section of second balun 1100 taken at outer ring wall 1126 of ring 1104 is identical to that taken at first slot end point 1118a except that first wall 1506 of tapered wall 1102 is replaced with outer ring wall 1126 of ring 1104.

With reference to FIG. 15C, a cross section of second balun 1100 taken at a point as indicated by 15C in FIG. 15A is shown in accordance with an illustrative embodiment. A first arc length 1512 defines an arc length between first slot wall 1120a and second slot wall 1122a of first tapered wall 1108a. An arc length (not shown) for second tapered wall 1108b is identical to first arc length 1512. Conductor width 1504 is identical between a first exterior surface 1508a and a first interior surface 1510a of first tapered wall 1108a and between a second exterior surface 1508b and a second interior surface 1510b of second tapered wall 1108b.

With reference to FIG. 15D, a cross section of second balun 1100 taken at first dipole arm wall 1115a and at second dipole arm wall 1115b as indicated by 15D in FIG. 15A is shown in accordance with an illustrative embodiment. A second arc length 1514 defines an arc length between first slot wall 1120a and second slot wall 1122a of first tapered wall 1108a for a cross section taken at first dipole arm wall 1115a. An arc length (not shown) for second tapered wall 1108b is identical to second arc length 1514 at first dipole arm wall 1115a. A prong arc length 1516 defines an arc length between first arm wall 1114a and second arm wall 1116a of second dipole arm 1106a and between third arm wall 1114b and fourth arm wall 1116b of third dipole arm 1106b.

With reference to FIG. 15E, a cross section of second balun 1100 taken at second wall 1520a, third wall 1520b, second dipole arm wall 1522a, and third dipole arm wall 1522b as indicated by 15E in FIG. 15A is shown in accordance with an illustrative embodiment. A minimum arc length 1518 defines an arc length between first slot wall 1120a and second slot wall 1122a of first tapered wall 1108a. An arc length (not shown) for second tapered wall 1108b is identical to minimum arc length 1518 at first dipole arm wall 1115a.

Figure 16:
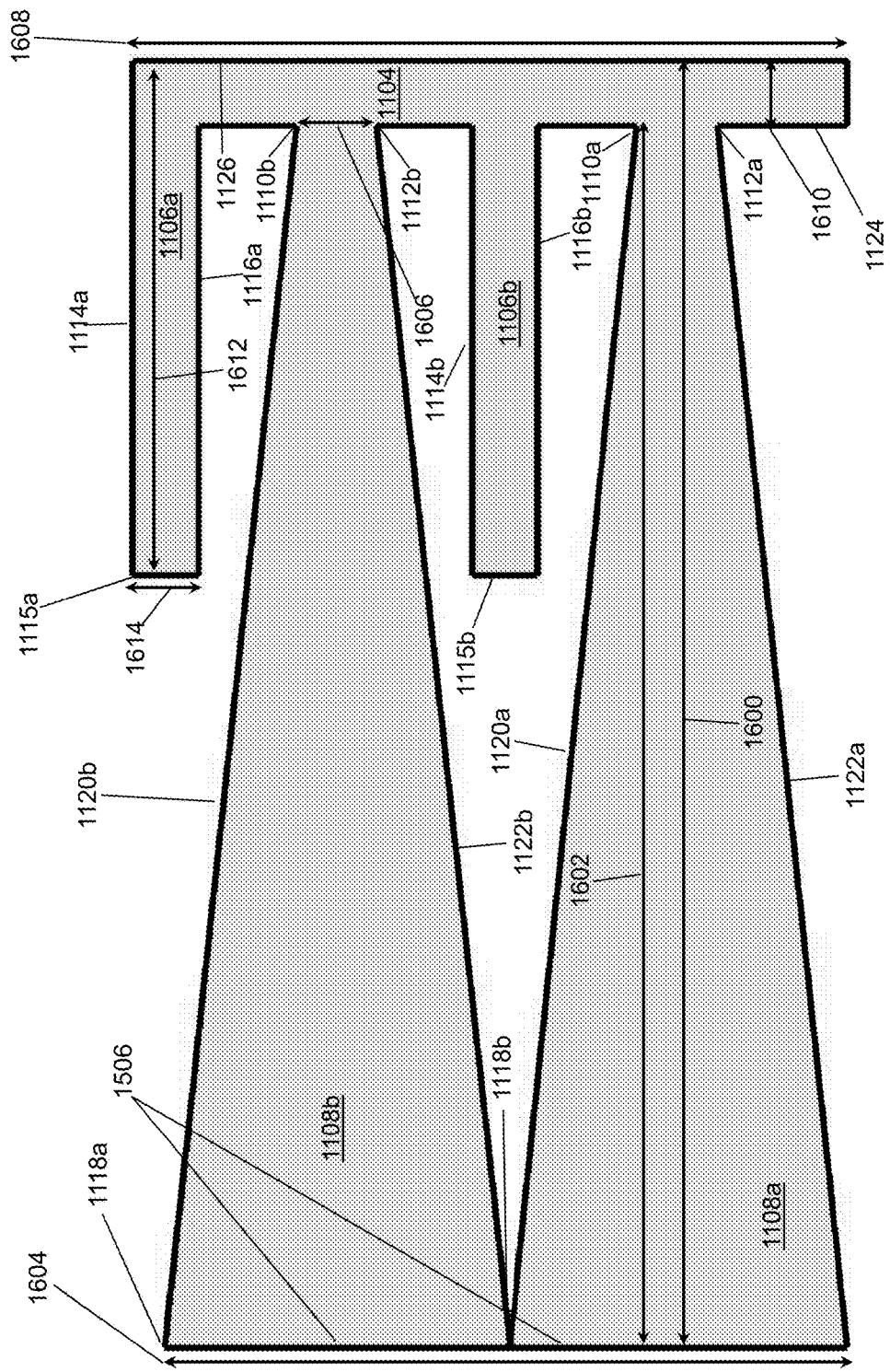
FIG. 16 depicts a top view of the MWA antenna system of FIGS. 11-14 unrolled and placed on a flat surface in accordance with an illustrative embodiment.

With reference to FIG. 16, a top view of second balun 1100 unrolled and placed on a flat surface is shown in accordance with an illustrative embodiment. A total length 1600 of second balun 1100 is measured between first wall 1506 and outer ring wall 1126 of ring 1104. A tapered wall length 1602 of first tapered wall 1108a and of second tapered wall 1108b is measured between first wall 1506 and second wall 1520a of first tapered wall 1108a and between first wall 1506 and fourth wall 1520b of second tapered wall 1108b, respectively. A tapered wall circumference 1604 defines a circumference of tapered wall 1102 at first slot end point 1115a. A tapered wall height 1606 is measured between first end point 1110a and second end point 1112a and defines a length of second wall 1520a of first tapered wall 1108a that mounts to inner ring wall 1124 of ring 1104. Tapered wall height 1606 also defines a length of third wall 1520b of second tapered wall 1108b that mounts to inner ring wall 1124 of ring 1104. A ring circumference 1608 defines a circumference of inner ring wall 1124 and outer ring wall 1126 of ring 1104. A ring width 1610 defines a width of ring 1104 measured between inner ring wall 1124 and outer ring wall 1126. A prong length 1612 is measured between first dipole arm wall 1115a and outer ring wall 330 of ring 1104 and includes ring width 1610. Prong length 1612 also defined a length between second dipole arm wall 1115b and outer ring wall 330 of ring 1104 and includes ring width 1610. A prong width 1614 defines a width of second dipole arm 1106a measured between first arm wall 1114a and second arm wall 1116a. A prong width 1614 defines a width of third dipole arm 1106b measured between third arm wall 1114b and fourth arm wall 1116b.

In the illustrative embodiment, when flattened, first slot wall 1120a, second slot wall 1122a, third slot wall 1120b, and fourth slot wall 1122b have a linear slope. In alternative embodiments, when flattened, first slot wall 1120a, second slot wall 1122a, third slot wall 1120b, and fourth slot wall 1122b may have different slopes that may be non-linear. For example, when flattened, first slot wall 1120a, second slot wall 1122a, third slot wall 1120b, and fourth slot wall 1122b may form a concave or convex curve between the slot wall end points. First slot wall 1120a and third slot wall 1120b have a same flattened shape. Second slot wall 1122a and fourth slot wall 1122b have a same flattened shape that is complementary to that of first slot wall 1120a and third slot wall 1120b.

Total length 1600 may be selected from a range defined by $$\frac{\lambda_0}{4} \text{ and } \frac{3\lambda_0}{2},$$

where $\lambda_0$ is the wavelength at the operating frequency of the signal carried by balun center conductor 326. Tapered wall height 1606, ring width 1610, and prong width 1614 may each be selected from a range defined by $$\frac{d}{2} \text{ and } 2 \times d,$$

where d is diameter 1500 of balun center conductor 326. Tapered wall height 1606, ring width 1610, and/or prong width 1614 may be equal. Prong length 1612 and dipole arm length 338 are selected from a range defined by $$\frac{\lambda_1}{4} \text{ and } \frac{\lambda_1}{2},$$

where $\lambda_1$ is an effective wavelength of an operating frequency of a signal carried by balun center conductor 326 in a medium defined by a tissue into which second balun 1100 and first dipole arm 100a are at least partially inserted. Tapered wall circumference 1604 and ring circumference 1608 may be equal to $2\pi r$, where $$r = \frac{d}{2} + d_d + d_c,$$

where $d_d$ equals dielectric width 1502, and $d_c$ equals conductor width 1504.

For illustration, the parameters of second balun 1100 and first dipole arm 100a to achieve localized specific absorption rate (SAR) and heating patterns and a good impedance match between antenna 100 and coaxial cable 102 at 6 GHz were again determined. The dimensions were determined as prong length 1612 equal to 8 mm, dipole arm length 1128 equal to 7 mm, total length 1600 equal to 18 mm, prong width 1614 equal to 0.7 mm, tapered wall height 1606 and ring width 1610 each equal to 0.5 mm, and tapered wall circumference 1604 and ring circumference 1608 each equal to π×2.2 mm, the outer circumference of coaxial cable 102. Coaxial cable 102 was selected as 50-Ω UT-085C semi-rigid cable. Copper tubing was used for second balun 1100. Polytetrafluoroethylene was used for balun dielectric material 334. Second balun 1100 and first dipole arm 100a were embedded in a polytetrafluoroethylene coating with a diameter of 2.6 mm.

Figure 17:
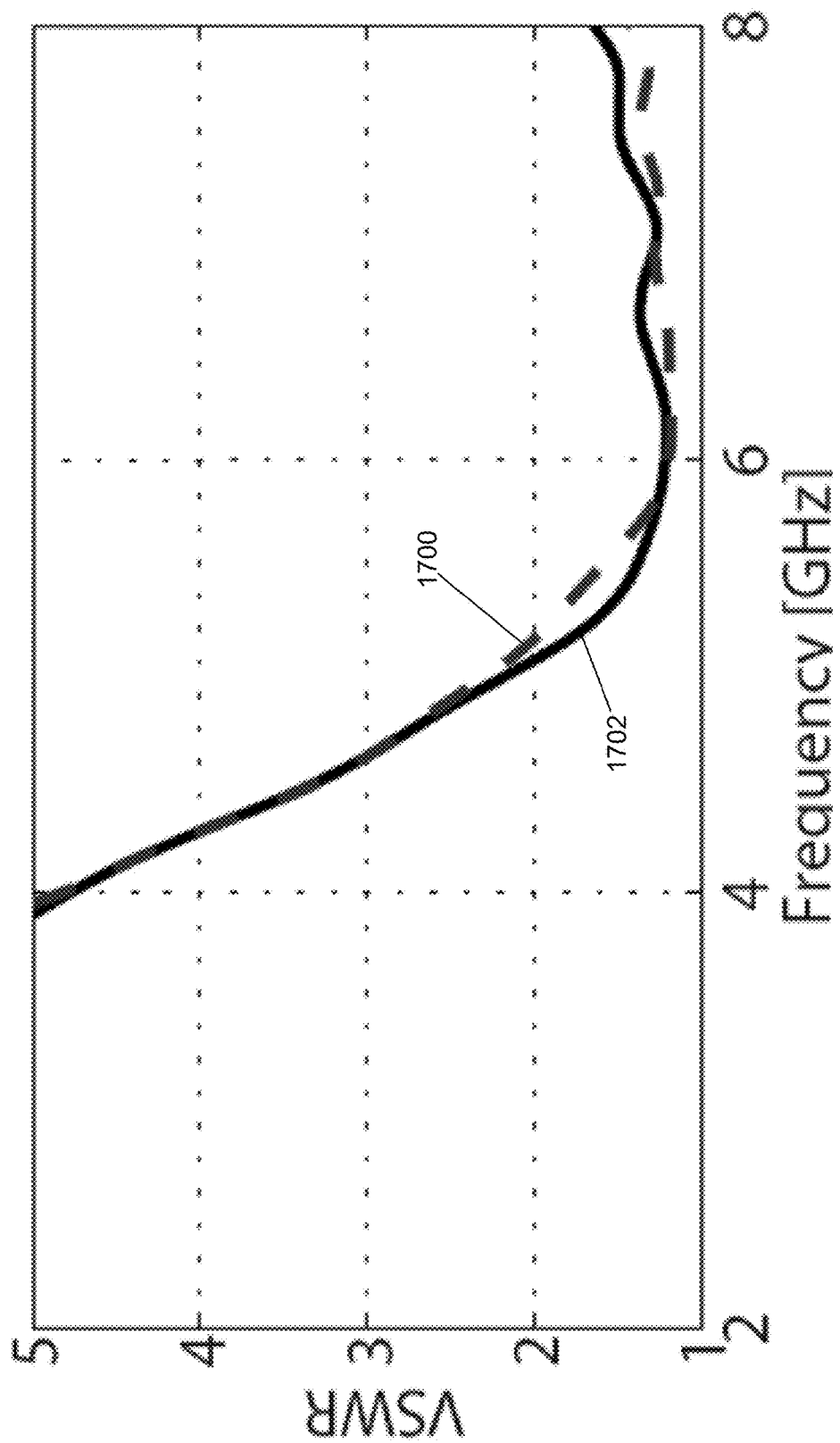
FIG. 17 shows a simulated and a measured voltage standing wave ratio as a function of frequency of the MWA antenna system illustrated in FIGS. 11-14 in accordance with an illustrative embodiment.
Figure 18:
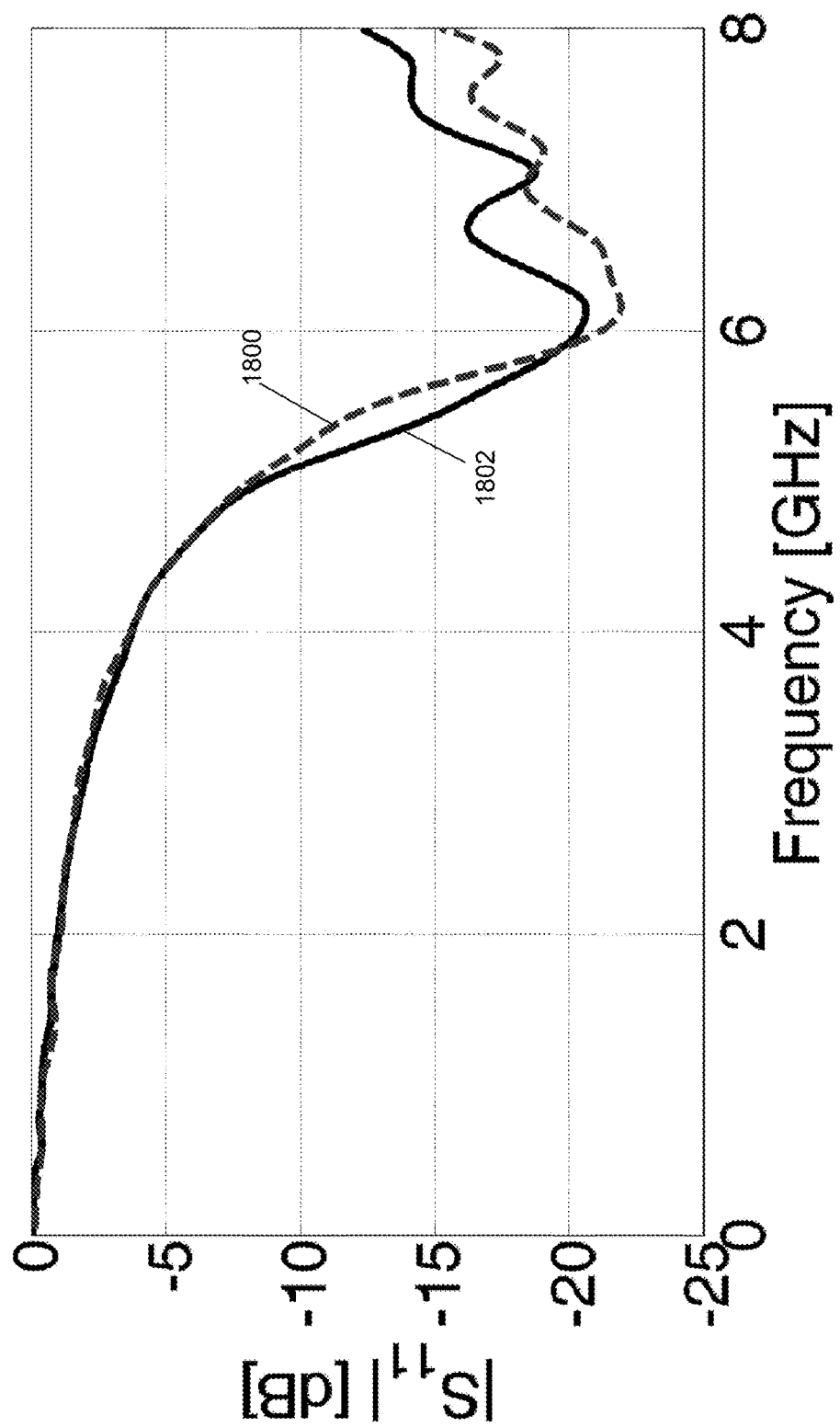
FIG. 18 shows a comparison between a simulated and a measured input reflection coefficient, $S_{11}$, of the MWA antenna system of FIGS. 11-14 in accordance with an illustrative embodiment.

Referring to FIG. 17, a measured VSWR curve 1700 and a simulated VSWR curve 1702 are shown. Referring to FIG. 18, a measured $|S_{11}|$ curve 1800 and a simulated $|S_{11}|$ curve 1802 are shown. The measured and simulated curves are in good agreement and show a good impedance match between antenna 100 and coaxial cable 102 over a wide frequency range (from 5 GHz to over 8 GHz). At the operating frequency of 6 GHz, the measured VSWR is 1.19 ($|S_{11}|$ of −22 dB), which is slightly better than the simulated values (VSWR=1.21, $|S_{11}|$=−20 dB). Additionally, the measured input impedance of antenna 100 was unchanged as the insertion depth of antenna 100 was varied as long as the entire second balun 1100 was immersed in liver with first dipole arm 100a. This confirmed that the outer surface currents were effectively suppressed along coaxial cable 102 up to a starting point of second balun 1100.

First dipole arm 100a with second balun 1100 achieved a slightly better impedance matching (VSWR=1.21, $|S_{11}|$=−20 dB) than first dipole arm 100a with first balun 300 (VSWR=1.38, $|S_{11}|$=−16 dB) at the operating frequency of 6 GHz. While increasing tapered wall length 1602 of first tapered wall 1108a and of second tapered wall 1108b may help reduce the reflection coefficient, the frequency of best impedance match is most sensitive to the dimensions of first dipole arm 100a, second dipole arm 1106a, and third dipole arm 1106b of the dipole and a thickness of the outermost coating, which in this case was 2.6 mm of polytetrafluoroethylene.

Figure 19:
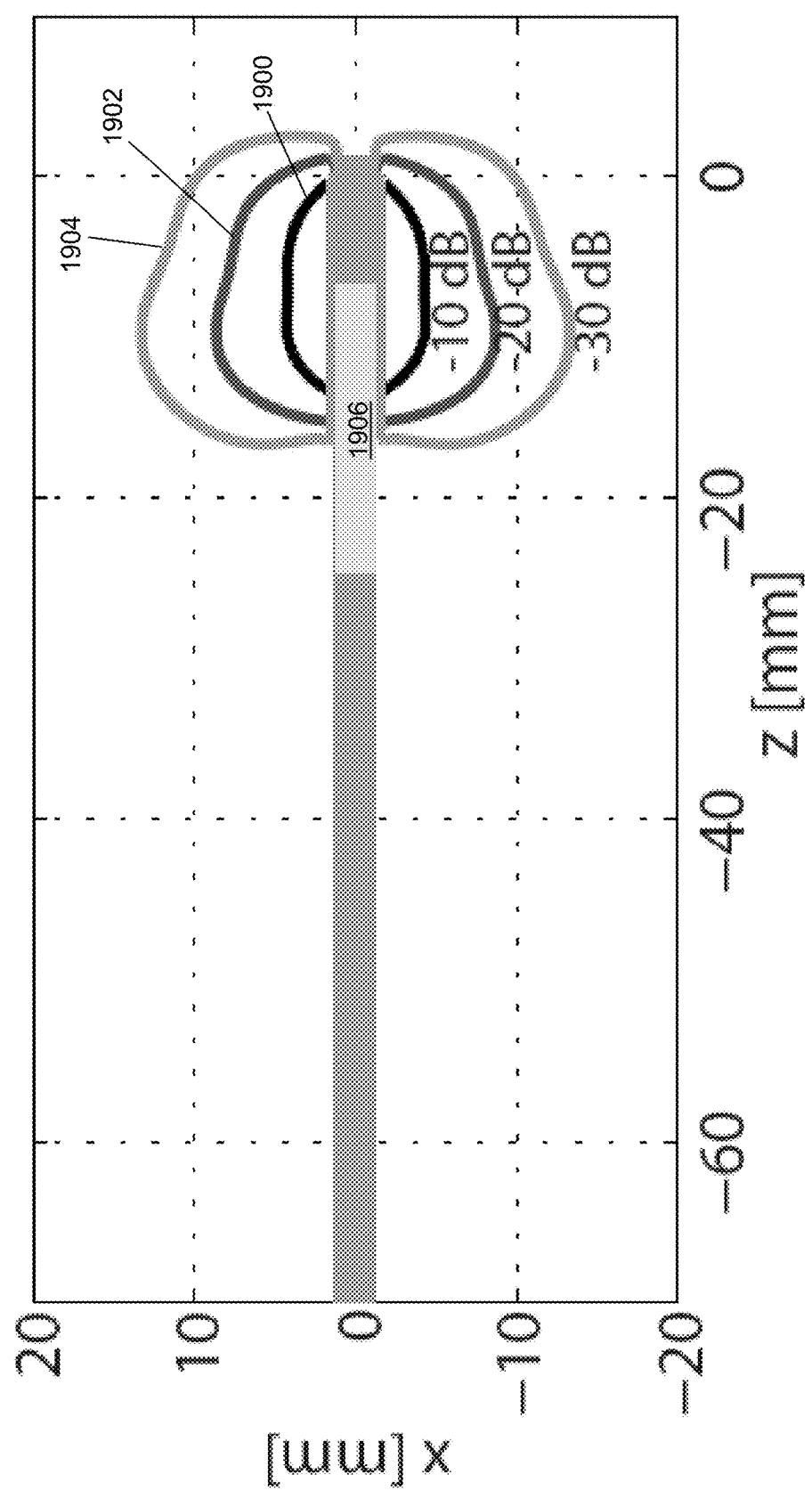
FIG. 19 shows a normalized SAR pattern of the MWA antenna system of FIGS. 11-14 in the x-z plane in accordance with an illustrative embodiment.
Figure 20:
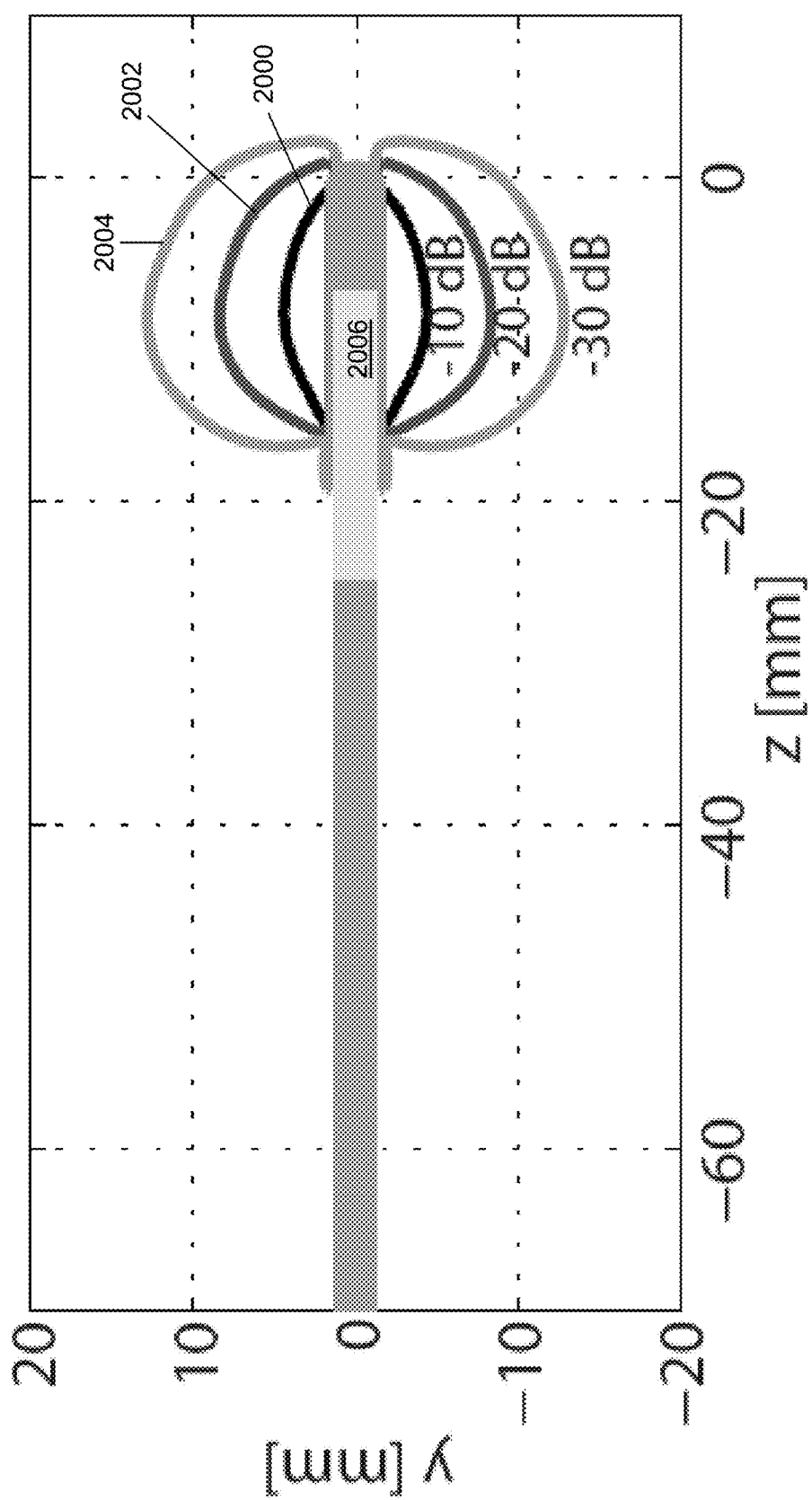
FIG. 20 shows a normalized SAR pattern of the MWA antenna system of FIGS. 11-14 in the y-z plane in accordance with an illustrative embodiment.

Referring to FIGS. 19 and 20, a normalized SAR pattern of antenna 100 with second balun 1100 is shown in the x-z and y-z planes, respectively, where z is along an axis of balun center conductor 326. The x-y planes define the cross sections of second balun 1100 with the x-axis and the y-axis as indicated in FIG. 5D. Referring to FIG. 19, a −10 dB curve 1900 shows a SAR level reduced by 10 dB compared to the maximum SAR level. A −20 dB curve 1902 shows a SAR level reduced by 20 dB compared to the maximum SAR level. A −30 dB curve 1904 shows a SAR level reduced by 30 dB compared to the maximum SAR level. A region 1906 indicates a location of second balun 1100 for reference.

Referring to FIG. 20, a −10 dB curve 2000 shows a SAR level reduced by 10 dB compared to the maximum SAR level. A −20 dB curve 2002 shows a SAR level reduced by 20 dB compared to the maximum SAR level. A −30 dB curve 2004 shows a SAR level reduced by 30 dB compared to the maximum SAR level. A region 2006 indicates a location of second balun 1100 for reference. The results indicate that the outer surface currents are effectively suppressed using second balun 1100, resulting in a compact SAR pattern with minimal tails along the shaft of coaxial cable 102. SAR values are reduced by 30 dB near first slot end point 1115a and second slot end point 1115b. First dipole arm 100a with second balun 1100 produced a highly compact volume enclosed by −30 dB curve 2004, of which the lateral diameter (about 26 mm) is even larger than the axial diameter (about 20 mm). Due to the lack of an axial symmetry, the SAR pattern in the x-z plane is slightly different from that in the y-z plane.

Figure 21:
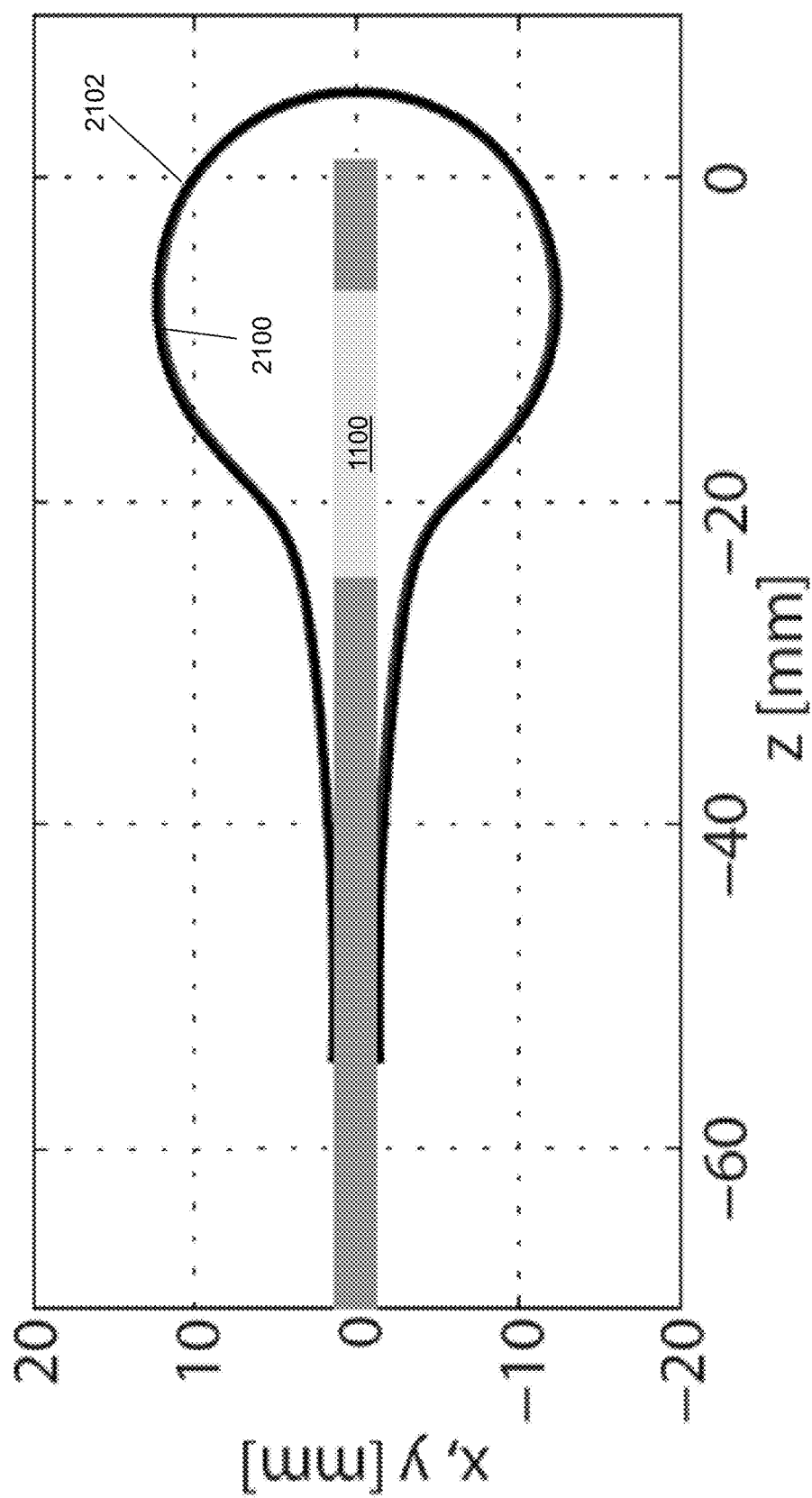
FIG. 21 shows a 50° Celsius contour after 5 minutes of ablation using the MWA antenna system of FIGS. 11-14 with 20 Watts of input power in the x-z and y-z planes in accordance with an illustrative embodiment.

Referring to FIG. 21, a simulated 50° C. contour, used to predict a boundary of an ablation zone, is shown in the x-z and the y-z planes at the end of a five minute ablation using an input power of 20 Watts (W). An x-z ablation zone 2100 and a y-z ablation zone 2102 are symmetrical. Despite a slight difference of the SAR pattern in the x-z (2100) and y-z (2102) planes, the ablation zone appears to be identical in these two cut planes, which demonstrates that first dipole arm 100a with second balun 1100 is capable of producing a rotationally symmetric ablation zone.

Compared to the antenna using the single-slot balun, SAR values less than −30 dB fall off faster along the shaft of second balun 1100. This is evident in the slightly longer tails of the −30 dB contours shown in −30 dB curve 804 and −30 dB curve 904 in comparison with −30 dB curve 1904 and −30 dB curve 2004. Moreover, first dipole arm 100a with second balun 1100 produced a symmetric SAR pattern in the y-z plane, as opposed to the asymmetric one in this cut plane of first dipole arm 100a with first balun 300. While thermal simulation results show that both provide ablation zones with similar dimensions, the one provided by first dipole arm 100a with second balun 1100 is more rotationally symmetric. Overall, the better impedance matching and more symmetric heating pattern make first dipole arm 100a with second balun 1100 a more desirable design for ablation applications where directional heating is not needed.

Figure 22:
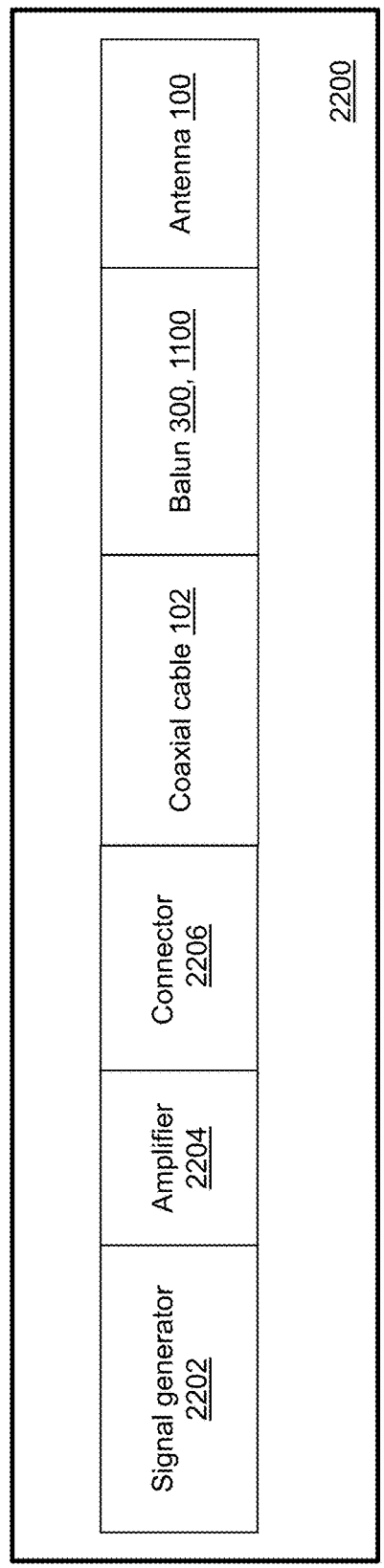
FIG. 22 depicts a block diagram of an MWA system including the balun of FIGS. 3 and 4 or of FIGS. 11-14 in accordance with an illustrative embodiment.

Referring to FIG. 22, a block diagram of a MWA system 2200 is shown in accordance with an illustrative embodiment. MWA system 2200 may include a signal generator 2202, an amplifier 2204, a connector 2206, coaxial cable 102, first balun 300 or second balun 1100, and antenna 100. For illustration, antenna 100 may include first dipole arm 100a and second dipole arm 1106a and third dipole arm 1106b. Signal generator 2202 generates an analog signal at the operating frequency selected for antenna 100. A duty cycle of the analog signal may be controlled by signal generator 2202 based, for example, on an ablation zone size and heating rate. The analog signal may be amplified by amplifier 2204. Connector 2206 connects a second end of coaxial cable 102 opposite first dipole arm 100a. The loss through coaxial cable 102 is considered when adjusting the output power level of amplifier 2204 for a desired input power level to first dipole arm 100a and second dipole arm 1106a and third dipole arm 1106b. Connector 2206 may be a coaxial connector designed to maintain the coaxial form across the connection and having the same impedance as coaxial cable 102.

Use of directional terms, such as top, bottom, right, left, front, back, upper, lower, horizontal, vertical, behind, etc. are merely intended to facilitate reference to the various surfaces of the described structures relative to the orientations introduced in the drawings and are not intended to be limiting in any manner unless otherwise indicated.

As used in this disclosure, the term "connect" includes join, unite, mount, couple, associate, insert, hang, hold, affix, attach, fasten, bind, paste, secure, bolt, screw, rivet, pin, nail, clasp, clamp, cement, fuse, solder, weld, glue, form over, slide together, layer, and other like terms. The phrases "connected on" and "connected to" include any interior or exterior portion of the element referenced. Elements referenced as connected to each other herein may further be integrally formed together. As a result, elements described herein as being connected to each other need not be discrete structural elements. The elements may be connected permanently, removably, or releasably.

As used in this disclosure, the term "mount" includes join, unite, connect, couple, associate, insert, hang, hold, affix, attach, fasten, bind, paste, secure, bolt, screw, rivet, pin, nail, clasp, clamp, cement, fuse, solder, weld, glue, form over, slide together, layer, and other like terms. The phrases "mounted on" and "mounted to" include any interior or exterior portion of the element referenced. These phrases also encompass direct connection (in which the referenced elements are in direct contact) and indirect connection (in which the referenced elements are not in direct contact, but are mounted together via intermediate elements). Elements referenced as mounted to each other herein may further be integrally formed together. As a result, elements described herein as being mounted to each other need not be discrete structural elements. The elements may be mounted permanently, removably, or releasably.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, using "and" or "or" in the detailed description is intended to include "and/or" unless specifically indicated otherwise.

The foregoing description of illustrative embodiments of the disclosed subject matter has been presented for purposes of illustration and of description. It is not intended to be exhaustive or to limit the disclosed subject matter to the precise form disclosed, and modifications and variations are possible in light of the above teachings or may be acquired from practice of the disclosed subject matter. The embodiments were chosen and described in order to explain the principles of the disclosed subject matter and as practical applications of the disclosed subject matter to enable one skilled in the art to utilize the disclosed subject matter in various embodiments and with various modifications as suited to the particular use contemplated. It is intended that the scope of the disclosed subject matter be defined by the claims appended hereto and their equivalents.

What is claimed is:

1. A balun comprising:
   a center conductor extending a length of the balun;
   a dielectric material surrounding the center conductor along the length of the balun;
   a tapered wall forming a portion of a tube between a first wall and a second wall, wherein the first wall is opposite the second wall, wherein the tapered wall is formed of a conductive material, wherein the portion of the tube forms a slot exposing the dielectric material;
   a ring connected to the second wall of the tapered wall, wherein the ring is formed of the conductive material, wherein the ring forms a tube surrounding the center conductor and the dielectric material; and
   a prong connected to the ring to extend toward the first wall, wherein the prong is formed of the conductive material, wherein the prong extends over a portion of the dielectric material exposed by the slot.

2. The balun of claim 1, wherein a length between the first wall and an outer wall of the ring is selected from a range defined by $$\frac{\lambda_1}{4} \text{ and } \frac{3\lambda_1}{2},$$

where $\lambda_1$ is a wavelength at an operating frequency of a signal carried by the center conductor, wherein the outer wall is opposite the second wall.

3. The balun of claim 2, wherein a width of the second wall is selected from a range defined by $$\frac{d}{2} \text{ and } 2 \times d,$$

where d is a diameter of the center conductor, wherein the width of the second wall is in a direction perpendicular to the length.

4. The balun of claim 1, wherein a length between a wall of the prong closest to the first wall and an outer wall of the ring is selected from a range defined by $\lambda_1/4$ and $\lambda_1/2$, where $\lambda_1$ is a wavelength at an operating frequency of a signal carried by the center conductor, wherein the outer wall is opposite the second wall.

5. The balun of claim 4, wherein a width of the prong is selected from a range defined by $$\frac{d}{2} \text{ and } 2 \times d,$$

where d is a diameter of the center conductor, wherein the width of the prong is in a direction perpendicular to the length.

6. The balun of claim 1, wherein a length between the second wall and an outer wall of the ring is selected from a range defined by $$\frac{d}{2} \text{ and } 2 \times d,$$

where d is a diameter of the center conductor, wherein the outer wall is opposite the second wall.

7. The balun of claim 1, wherein a circumference of the ring is equal to a length of the first wall.

8. The balun of claim 1, further comprising:
   a second tapered wall forming a second portion of the tube between a third wall and a fourth wall, wherein the second tapered wall is formed of the conductive material, wherein the second portion of the tube forms a second slot exposing the dielectric material, wherein the ring is connected to the fourth wall of the second tapered wall, wherein the third wall is opposite the fourth wall; and a second prong connected to the ring to extend toward the third wall, wherein the second prong is formed of the conductive material, wherein the second prong extends over a second portion of the dielectric material exposed by the second slot.

9. The balun of claim 8, wherein a length between the first wall and an outer wall of the ring is selected from a range defined by $$\frac{\lambda_1}{4} \text{ and } \frac{3\lambda_1}{2},$$

where $\lambda_1$ is a wavelength at an operating frequency of a signal carried by the center conductor, wherein the outer wall is opposite the second wall, wherein a second length between the third wall and the outer wall of the ring is equal to the length.

10. The balun of claim 9, wherein a width of the second wall is selected from a range defined by $$\frac{d}{2} \text{ and } 2 \times d,$$

where d is a diameter of the center conductor, wherein the width of the second wall is in a direction perpendicular to the length, wherein a width of the fourth wall is equal to the width of the second wall.

11. The balun of claim 8, wherein a length between a wall of the prong closest to the first wall and an outer wall of the ring is selected from a range defined by $\lambda_1/4$ and $\lambda_1/2$, where $\lambda_1$ is a wavelength at an operating frequency of a signal carried by the center conductor, wherein the outer wall is opposite the second wall, wherein a second length between a wall of the second prong closest to the third wall and the outer wall of the ring is equal to the length.

12. The balun of claim 11, wherein a width of the prong is selected from a range defined by $$\frac{d}{2} \text{ and } 2 \times d,$$

where d is a diameter of the center conductor, wherein the width of the prong is in a direction perpendicular to the length, wherein a width of the second prong is equal to the width of the prong.

13. The balun of claim 8, wherein a length between the second wall and an outer wall of the ring is selected from a range defined by $$\frac{d}{2} \text{ and } 2 \times d,$$

where d is a diameter of the center conductor, wherein the outer wall is opposite the second wall.

14. The balun of claim 8, wherein a circumference of the ring is equal to a length of the first wall plus the third wall.

15. An antenna system comprising:
a coaxial cable comprising
a center conductor extending a length of the coaxial cable;
a dielectric material surrounding the center conductor along the length of the coaxial cable; and
a conductive shield surrounding the dielectric material along the length of the coaxial cable;
a first dipole arm connected to the center conductor; and
a balun connected between an end of the coaxial cable and the first dipole arm, the balun comprising
a second center conductor extending a length of the balun, the second center conductor connected to and extending from the center conductor between the center conductor and the first dipole arm;
a second dielectric material surrounding the second center conductor along the length of the balun;
a tapered wall forming a portion of a tube between a first wall and a second wall, wherein the first wall is opposite the second wall, wherein the first wall is connected to the conductive shield, wherein the tapered wall is formed of a conductive material, wherein the portion of the tube forms a slot exposing the second dielectric material;
a ring connected to the second wall of the tapered wall, wherein the ring is formed of the conductive material, wherein the ring forms a tube surrounding the second center conductor and the second dielectric material; and
a prong connected to the ring to extend toward the first wall, wherein the prong is formed of the conductive material, wherein the prong extends over a portion of the second dielectric material exposed by the slot and forms a second dipole arm.

16. The antenna system of claim 15, wherein the second center conductor is formed as an extension of the center conductor.

17. The antenna system of claim 16, wherein the first dipole arm is formed as an extension of the second center conductor.

18. The antenna system of claim 15, wherein a length between the first wall and an outer wall of the ring is selected from a range defined by $$\frac{\lambda_1}{4} \text{ and } \frac{3\lambda_1}{2},$$

where $\lambda_1$ is a wavelength at an operating frequency of a signal carried by the center conductor, wherein the outer wall is opposite the second wall.

19. The antenna system of claim 15, wherein a length between a wall of the prong closest to the first wall and an outer wall of the ring is selected from a range defined by $\lambda_1/4$ and $\lambda_1/2$, where $\lambda_1$ is a wavelength at an operating frequency of a signal carried by the center conductor, wherein the outer wall is opposite the second wall.

20. The antenna system of claim 15, wherein a length of the first dipole arm is selected from a range defined by $\lambda_1/4$ and $\lambda_1/2$, where $\lambda_1$ is a wavelength at an operating frequency of a signal carried by the center conductor.

* * * * *

UNITED STATES PATENT AND TRADEMARK OFFICE
CERTIFICATE OF CORRECTION

PATENT NO.        : 10,492,860 B2
APPLICATION NO.   : 15/454218
DATED             : December 3, 2019
INVENTOR(S)       : Susan C. Hagness et al.

Page 1 of 2

It is certified that error appears in the above-identified patent and that said Letters Patent is hereby corrected as shown below:

In the Specification

Column 4, Line 21:
Delete the phrase "defined as $\lambda_o = c/F_o$," and replace with --defined as $\lambda_o = c/f_o$,--.

Column 4, Line 23:
Delete the phrase "and $f_o$ is the selected" and replace with --and $f_o$ is the selected--.

Column 8, Line 57:
Delete the phrase "10.75 mm for the upper side ($r_i$)" and replace with --10.75 mm for the upper side ($r_1$)--.

In the Claims

Claim 4, Column 16, Line 32:
Delete the phrase "a range defined by $\lambda_1/4$ and $\lambda_1/2$," and replace with --a range defined by $\frac{\lambda_1}{4}$ and $\frac{\lambda_1}{2}$,--.

Claim 11, Column 17, Line 33:
Delete the phrase "a range defined by $\lambda_1/4$ and $\lambda_1/2$," and replace with --a range defined by $\frac{\lambda_1}{4}$ and $\frac{\lambda_1}{2}$,--.

Claim 19, Column 18, Line 54-55:
Delete the phrase "a range defined by $\lambda_1/4$ and $\lambda_1/2$," and replace with --a range defined by $\frac{\lambda_1}{4}$ and $\frac{\lambda_1}{2}$,--.

Signed and Sealed this
Seventeenth Day of March, 2020

Andrei Iancu
*Director of the United States Patent and Trademark Office*

Claim 20, Column 18, Line 59-60:
Delete the phrase "a range defined by $\lambda_1/4$ and $\lambda_1/2$," and replace with --a range defined by $\frac{\lambda_1}{4}$ and $\frac{\lambda_1}{2}$,--.